US008821845B2

(12) United States Patent
Seigneurin et al.

(10) Patent No.: US 8,821,845 B2
(45) Date of Patent: *Sep. 2, 2014

(54) CONCENTRATED INGREDIENT FOR TREATING AND/OR MODIFYING SURFACES, AND USE THEREOF IN COSMETIC COMPOSITIONS

(75) Inventors: Aline Seigneurin, Le Chesnay (FR); Carole Foucault, Charenton le Pont (FR); Anne-Gaelle Dreno, Sevran (FR)

(73) Assignee: Rhodia Chimie, Aubervilliers (FR)

( * ) Notice: Subject to any disclaimer, the term of this patent is extended or adjusted under 35 U.S.C. 154(b) by 1168 days.

This patent is subject to a terminal disclaimer.

(21) Appl. No.: 11/474,193

(22) Filed: Jun. 23, 2006

(65) Prior Publication Data

US 2007/0148116 A1    Jun. 28, 2007

(30) Foreign Application Priority Data

Jun. 23, 2005   (FR) ..................................... 05 06385

(51) Int. Cl.
*A61K 8/81*        (2006.01)
*A61Q 5/12*        (2006.01)

(52) U.S. Cl.
CPC .. *A61K 8/817* (2013.01); *A61Q 5/12* (2013.01)
USPC ..................................................... 424/70.21

(58) Field of Classification Search
None
See application file for complete search history.

(56) References Cited

U.S. PATENT DOCUMENTS

| | | |
|---|---|---|
| 2,254,239 A | 9/1941 | William |
| 3,308,067 A | 3/1967 | Diehl |
| 3,893,929 A | 7/1975 | Basadur |
| 3,912,808 A | 10/1975 | Sokol |
| 3,959,230 A | 5/1976 | Hays |
| 4,116,896 A | 9/1978 | Garrett et al. |
| 4,333,921 A | 6/1982 | Luedicke et al. |
| 4,387,017 A | 6/1983 | McEntire et al. |
| 4,565,647 A | 1/1986 | Llenado |
| 4,597,898 A | 7/1986 | Vander Meer |
| 4,610,874 A | 9/1986 | Matravers |
| 4,701,322 A | 10/1987 | Dixon et al. |
| 4,711,730 A | 12/1987 | Gosselink et al. |
| 4,721,580 A | 1/1988 | Gosselink |
| 4,746,456 A | 5/1988 | Kud et al. |
| 4,770,666 A | 9/1988 | Clauss |
| 4,832,872 A | 5/1989 | Scandel |
| 4,877,896 A | 10/1989 | Maldonado et al. |
| 4,906,460 A | 3/1990 | Kim et al. |
| 4,968,451 A | 11/1990 | Scheibel et al. |
| 5,041,282 A | 8/1991 | Sabatelli et al. |
| 5,290,631 A | 3/1994 | Fleury et al. |
| 5,554,313 A | 9/1996 | Chandler |
| 6,010,690 A | 1/2000 | Varco |
| 6,294,160 B1 | 9/2001 | Decoster |
| 6,673,371 B2 | 1/2004 | Brown et al. |
| 6,696,051 B2* | 2/2004 | Barbuzzi et al. ........... 424/70.12 |
| 6,846,785 B2 | 1/2005 | Patel |
| 2003/0211069 A1* | 11/2003 | Deckner et al. ............ 424/70.16 |
| 2003/0223951 A1* | 12/2003 | Geary et al. ................ 424/70.17 |
| 2004/0013638 A1 | 1/2004 | Aubay et al. |
| 2004/0234482 A1 | 11/2004 | Muller et al. |
| 2005/0191265 A1* | 9/2005 | Seigneurin et al. ........ 424/70.16 |

FOREIGN PATENT DOCUMENTS

| | | |
|---|---|---|
| EP | 0066915 | 12/1982 |
| EP | 0011984 | 8/1983 |
| EP | 0156646 | 10/1985 |
| EP | 04320951 A2 | 6/1991 |
| EP | 0529883 A1 | 3/1993 |
| EP | 0540374 | 5/1993 |
| EP | 0904045 | 3/1999 |
| FR | 2236926 | 7/1972 |
| FR | 2334698 | 8/1977 |
| FR | 2728915 | 7/1996 |
| GB | 1475798 | 6/1977 |
| GB | 1578930 | 11/1980 |
| WO | WO 92/16187 | 10/1992 |
| WO | WO 98/26036 | 6/1998 |
| WO | WO 99/37279 | 7/1999 |
| WO | WO 01/10213 | 2/2001 |
| WO | WO 2004/084844 | 10/2004 |

OTHER PUBLICATIONS

Robinson; "Viscosity-molecular weight relationships, intrinsic chain flexibility, and dynamic solution properties of guar galactomannan"; Carbohydrate Research © 1982; vol. 107, pp. 17-32.
Hutter, Journal of the Society of Cosmetic Chemists, vol. 42, pp. 87-96, Mar.-Apr. 1991.
Ingredients—Shampoo http://web/20031105190602/http://sci-toys.com/ingredients/shampoo.html as archived in Nov. 5, 2003 by the Internet Archive Wayback Machine Accessed Jan. 3, 2009.

* cited by examiner

*Primary Examiner* — Brian Gulledge
(74) *Attorney, Agent, or Firm* — Hunton & Williams LLP

(57) ABSTRACT

The present invention relates to a concentrated ingredient for treating and/or modifying surfaces, especially for treating and/or modifying the skin and/or the hair. The invention also relates to the use of this ingredient in cosmetic compositions, for example in shampoos, shower gels or leave-in or rinse-out hair conditioners. The ingredient comprises a conditioning agent and a polymer for aiding deposition.

25 Claims, No Drawings

CONCENTRATED INGREDIENT FOR TREATING AND/OR MODIFYING SURFACES, AND USE THEREOF IN COSMETIC COMPOSITIONS

CROSS-REFERENCE TO RELATED APPLICATIONS

This application claims the benefit of French Application No, FR 05 06385, filed Jun. 23, 2005.

The present invention relates to a concentrated ingredient for treating and/or modifying surfaces, especially for treating and/or modifying the skin and/or the hair. The invention also relates to the use of this ingredient in cosmetic compositions, for example in shampoos, shower gels or rinse-out or leave-in hair conditioners.

Compositions for treating and/or modifying surfaces, for example cosmetic compositions, are made from mixed ingredients in order to give the composition the desired use. The functions and properties of the compositions are thus associated with the ingredients present in the composition, and/or with their mutual interactions, and/or with their interactions with the surface and/or interactions during the modification of a parameter, for instance the pH, the dilution or the temperature.

It is known practice to use cationic polymers, especially cationic polysaccharides, in cosmetic compositions, in particular in shampoos. These ingredients may afford modified rheology, and/or stabilization, and/or conditioning of the skin and/or the hair. Cationic polymers that are useful are, for example, cationic guars or cationic cellulose derivatives.

It is known practice to use conditioning agents in shampoos, especially polyorganosiloxanes.

It is known practice to combine conditioning agents such as polyorganosiloxanes with cationic polymers, in cosmetic compositions. The preparation of cosmetic compositions by separately adding a conditioning agent, cationic polymers and other ingredients has thus been described. Combinations of polyorganosiloxanes and of cationic polymers are described, for example, in documents EP 432 951, EP 529 883 and EP 904 045. Such combinations have been described as being advantageous as regards the stability of the compositions and as regards the hair conditioning properties. It has been taught that the conditioning may be linked to a deposition of matter on the hair. It has also been taught that the deposition of conditioning agents may be linked to phenomena of formation and/or destabilization of coacervates between the cationic polymer and anionic surfactants during the application of the composition and/or of its rinsing.

It is still sought, especially in cosmetic compositions for treating the skin and/or the hair, to optimize certain properties, for instance the viscosity, the transparency or the deposition of matter (conditioning effect), and/or, more generally, to optimize cosmetic effects such as the softness, suppleness, disentangling, sheen or styleability on dry or wet hair. Needless to say, besides the effects afforded by the ingredients, formulations that are easy to prepare, easy to use and sufficiently stable are also sought.

It is still sought to propose novel ingredients, which are useful especially for cosmetic compositions, which are in particular intended to be rinsed out, and which have improved qualities in terms of stability and/or simplification of the formulations and/or cosmetic qualities (mentioned above) and/or deposition of matter (deposition of a polymer bearing cationic charges or deposition of other matter, for instance animal, mineral, plant or synthetic oils, for example silicone oils, or "polyorganosiloxanes").

The object of the invention is to satisfy the needs mentioned above by proposing a concentrated ingredient for treating and/or modifying surfaces, comprising the following products:
a) a conditioning agent,
b) a polymer for aiding deposition,
c) optionally a surfactant, and
d) optionally water,
characterized in that:
   the total weight amount of products a) and b) in the ingredient is at least 10%, preferably at least 20%, preferably at least 50% and preferably at least 60%, and
   the weight ratio between product c), if it is present, and product a) is less than 1, preferably less than 0.5 and preferably less than 0.1.

A subject of the invention is also the use of the ingredient in cosmetic compositions.

A subject of the invention is also a process for preparing cosmetic compositions, comprising a step of mixing the ingredient with other products, especially a cosmetically acceptable vector.

A subject of the invention is also a process for preparing cosmetic compositions, comprising a step of preparing the ingredient and then a step of mixing the ingredient with other products, especially a cosmetically acceptable vector.

A subject of the invention is also a process for treating and/or modifying surfaces, preferably the skin and/or the hair, comprising a step of applying a composition comprising the concentrated ingredient, preferably a cosmetic composition, and a step of applying the composition to the surface.

It is found that the use of the concentrated ingredient comprising the conditioning agent and the polymer for aiding deposition makes it possible to substantially modify the conditioning properties, especially to increase the deposition, of a composition into which it is introduced, when compared with the use of a combination of the products of the ingredient, by introduction separately into the composition.

Formulation and Form of the Ingredient

The concentrated ingredient may be in solid or liquid (fluid) form. When it is in liquid form, it may be a solution, a dispersion of solid particles in a liquid phase or an emulsion or microemulsion comprising an inner liquid phase dispersed in an outer liquid phase. It may especially be an emulsion in an outer aqueous phase. Thus, it may be a concentrated ingredient comprising water, in the form of a direct emulsion comprising droplets of the conditioning agent a) dispersed in water.

In the concentrated ingredient, the weight amount of water is less than 90% by weight and preferably less than 75% by weight. This amount may even be less than 50% by weight, and even zero.

The weight ratio between product b) and product a) in the concentrated ingredient is preferably between 0.05 (5/100) and 9 (90/10), preferably between 0.05 and 0.5 (25/50), and preferably between 0.075 and 0.3.

The ingredient advantageously comprises:
   from 10% to 75% by weight and preferably from 20% to 70% by weight of product a),
   from 0.5% to 20% by weight and preferably from 1% to 15% by weight of product b),
   from 0 to 15% by weight of product c), and
   optionally water.

It is mentioned that the concentrated ingredient may also comprise an active agent intended to produce an effect on the skin and/or the hair. Such an agent may be, for example, antidandruff agents, UV-protecting agents or coloration-protecting agents. These active agents may be organic compounds or mineral particles. If they are included in the concentrated ingredient, the active agents may be dispersed in the conditioning agent a):

- as a solution, optionally with a cosolvent for the agent and the active agent,
- as a dispersion of solid particles, or
- as an emulsion dispersed in the form of droplets in the conditioning agent or in a solution comprising the conditioning agent.

The concentrated ingredient may thus be a multiple emulsion comprising an outer aqueous phase, an intermediate phase, dispersed in the outer phase, comprising the conditioning agent, and an inner phase dispersed in the intermediate phase, comprising the active agent.

The active agent may thus be vectorized by the conditioning agent on the skin and/or the hair.

In the concentrated ingredient, the overall charge of the polymer for aiding deposition, and its solubility or stability, may vary depending on the pH. Preferably, the pH is such that the overall charge is positive or neutral.

The ingredient is preferably different than an ingredient comprising a combination of polyvinylpyrrolidone (PVP) or of a copolymer of PVP and of MAPTAC (polyquaternium-28) and of a fluid silicone, in a weight ratio of polymer to silicone of greater than or equal to 90/10.

The ingredient is preferably different than an ingredient comprising a silicone oil and succinoglycan.

Conditioning Agent a)

The concentrated ingredient comprises at least one conditioning agent. It is not excluded for it to comprise a mixture or combination of such agents.

The conditioning agent a) is advantageously a water-insoluble nonvolatile oil.

The conditioning agent may be chosen especially from:
- a1) plant, mineral or animal oils, or derivatives thereof, and
- a2) polyorganosiloxanes.

Among the plant oils and derivatives thereof that may especially be mentioned are: Almond oil (sweet almond oil), anhydrous lanolin oil, apricot kernel oil, avocado oil, castor oil, jojoba oil, olive oil, groundnut oil, sesame seed oil, sunflower oil, corn oil, cottonseed oil, hydrogenated vegetable oils, soybean oil, sulfonated castor oil, coconut oil, cocoa butter, wheatgerm oil, aloe vera, grapeseed oil, hazelnut oil, macadamia nut oil, St-Jean protuberance oil, walnut oil, hazelnut oil, borage oil, peach kernel oil, virgin coconut oil, baobab oil, avocado butter, palm oil, palm kernel oil, flax oil, copra oil and babassu oil.

Among the oils of animal origin that may be mentioned, inter alia, are sperm whale oil, whale oil, seal oil, sardine oil, herring oil, shark oil, cod liver oil; pig fat or sheep fat (tallow).

As regards mineral oils, mention may be made, inter alia, of naphthenic oils and paraffinic oils (petroleum jelly or petrolatum). Mention may also be made of perhydrosqualene and squalene.

The ingredient may comprise a silicone (silicone oil). The terms "silicone" and "polyorganosiloxane" mean any organosiloxane compound comprising alkyl groups (for example methyl) and/or functionalized with groups other than alkyl groups.

The polyorganosiloxane is advantageously (in shampoos and hair conditioners in particular) a nonvolatile water-insoluble polyorganosiloxane. It advantageously has a viscosity of between 1000 and 2 000 000 mPa·s and preferably between 5000 and 1 000 000 mPa·s (at 25° C.). The polyorganosiloxane may especially be a polydimethylorganosiloxanesiloxane ("PDMS", INCI name: dimethicone) or a polyorganosiloxane containing amine groups (for example Amodimethicone according to the INCI name), quaternary ammonium groups (for example the silicones Quaternium 1 to 10 according to the INCI name), hydroxyl groups (terminal or nonterminal), polyoxyalkylene groups, for example polyethylene oxide and/or polypropylene oxide (as end groups, as a block in a PDMS chain, or as grafts) or aromatic groups, or several of these groups.

The polyorganosiloxanes that are useful in the cosmetics field and the characteristics thereof are known to those skilled in the art.

The polyorganosiloxanes (silicones) are preferably present in the concentrated ingredient in emulsion form (liquid droplets of silicone dispersed in the aqueous phase). The emulsion may especially be an emulsion with a mean droplet size of greater than or equal to 2 µm, or with a mean droplet size of between 0.15 µm and 2 µm, or with a mean droplet size of less than or equal to 0.15 µm.

The droplets of the emulsion may be of more or less large size. Reference may thus be made to microemulsions, miniemulsions or macroemulsions. In the present patent application, the term "emulsion" especially covers all, these types of emulsion. Without wishing to be bound to any theory, it is pointed out that microemulsions are generally thermodynamically stable systems, generally comprising large amounts of emulsifiers such as surfactants c). The other emulsions are generally systems in thermodynamically unstable state, conserving for a certain time, in metastable state, the mechanical energy supplied during the emulsification. These systems generally comprise smaller amounts of emulsifiers.

The emulsions may be obtained by mixing an outer phase, which is preferably aqueous, polyorganosiloxane, polymer for aiding deposition and, in general, an emulsifier, followed by emulsification. This process may be referred to as in-situ emulsification.

The microemulsion droplet size may be measured on an emulsion prepared prior to its introduction into the cosmetic composition, by dynamic light scattering (DQEL), for example as described below. The apparatus used consists, for example, of a Spectra-Physics 2020 laser, a Brookhaven 2030 correlator and the associated computerware. Since the sample is concentrated, it is diluted in deionized water and filtered through a 0.22 µm filter in order finally to be at 2% by weight. The diameter obtained is an apparent diameter. The measurements are taken at angles of 90° and 135°. For the size measurements, besides the standard cumulative analysis, three exploitations of the self-correlation function are used (exponential sampling or EXPSAM described by Prof. Pike, the "nonnegatively constrained least squares" or NNLS method, and the CONTIN method described by Prof. Provencher), which each give a size distribution weighted by the scattered intensity, rather than by the mass or the number. The refractive index and the viscosity of water are taken into account.

According to one useful embodiment, the concentrated ingredient is transparent. It may, for example, have a transmittance of at least 90% and preferably of at least 95%, at a wavelength of 600 nm, for example measured using a Lambda 40 UV-Vis spectrometer, at a concentration of 0.5% by weight in water. In this context, the cosmetic composition in which it will be used may advantageously be transparent. It may have, for example, a transmittance of at least 90% and preferably of at least 95%, at a wavelength of 600 nm, for example measured using a Lambda 40 UV-Vis spectrometer.

According to another particular embodiment, the concentrated ingredient is an emulsion whose mean droplet size is greater than or equal to 0.15 µm, for example greater than 0.5 µm, or 1 µm, or 2 µm, or 10 µm, or 20 µm, and preferably less than 100 µm. The droplet size may be measured on an emulsion prepared prior to its introduction into the cosmetic composition, by optical microscopy and/or laser granulometry (Horiba LA-910 laser scattering analyzer). In this embodiment, the composition in which the ingredient will be used preferably comprises a proportion of less than 10% by weight of emulsifier relative to the weight of polyorganosiloxane.

Among the water-soluble silicones of the composition that may be mentioned, inter alia, are dimethicone copolyols (Mirasil DMCO sold by the company Rhodia Chimie).

As regards silicones in the form of water-insoluble dispersions or emulsions, nonvolatile water-insoluble organopolysiloxanes may appropriately be used, among which mention may be made of polyalkylsiloxane, polyarylsiloxane, and polyalkylarylsiloxane oils, gums or resins or nonvolatile water-insoluble functionalized derivatives thereof, or mixtures thereof.

Said organopolysiloxanes are considered as being water-insoluble and nonvolatile when their solubility in water is less than 50 g/liter and their intrinsic viscosity is at least 3000 mPa·s, at 25° C.

Examples of nonvolatile water-insoluble organopolysiloxanes or silicones that may be mentioned include silicone gums, for instance the diphenyl dimethicone gum sold by the company Rhodia Chimie, and preferably polydimethylorganosiloxanes with a viscosity at least equal to $6 \times 10^5$ mPa·s, at 25° C., and even more preferentially those with a viscosity of greater than $2 \times 10^6$ mPa·s, at 25° C., such as Mirasil DM 500000® sold by the company Rhodia Chimie.

According to the invention, the nonvolatile water-insoluble organopolysiloxane or silicone is in a form dispersed in the concentrated ingredient containing it.

Among these low-viscosity silicones, mention may be made of cyclic volatile silicones and polydimethylorganosiloxanes of low mass.

It is also possible to use functionalized silicone derivatives, for instance amine derivatives directly in the form of emulsions or starting with a preformed microemulsion. These may be compounds known as amino silicones or hydroxyl silicones. Mention is made, for example, of the oil Rhodorsil amine 21637 (Amodimethicone) sold by the company Rhodia, and dimethiconol.

As polyorganosiloxanes that may be used mention is made especially of:
- polyorganosiloxanes comprising units —Si(CH$_2$)$_2$O— and units —SiY(CH$_2$)O— in which Y is a —(CH$_2$)$_3$—NH(CH$_2$)$_2$—NH$_2$ or —(CH$_2$)$_3$—NH$_2$ group,
- polyorganosiloxanes comprising units —Si(CH$_2$)$_2$O— and end units —HO—Si(CH$_2$)$_2$O— and/or non-end units —Si(CH$_2$)(OH)O—
- polyorganosiloxanes comprising units —Si(CH$_2$)$_2$O— and units —SiY(CH$_2$)O— in which Y is -L$^x$-Z$^x$-Palk in which L$^x$ is a divalent bonding group, preferably an alkyl group, Z$^x$ is a covalent bond or a divalent connecting group comprising a heteroatom, Palk is a group of formula [OE]$_s$-[OP]$_t$—X', in which OE is a group of formula —CH$_2$—CH$_2$—O—, OP is a group of formula —CH$_2$—CHCH$_3$—O— or —CHCH$_3$—CH$_2$—O—, X' is a hydrogen atom or a hydrocarbon-based group, s is a mean number greater than 1, and t is a mean number greater than or equal to 0,
- polyorganosiloxanes whose chain comprises at least one block comprising units of formula —Si(CH$_2$)$_2$O— and at least one block [OE]$_s$-[OP]$_t$—,
- polyorganosiloxanes comprising units —Si(CH$_2$)$_2$O— and/or units —Si(CH$_2$)RO— and/or —SiR$_2$O— and/or R—Si(CH$_2$)$_2$O— and/or H$_3$C—SiR$_2$O— and/or R—SiR$_2$O— in which R, which may be identical or different, is an alkyl group other than a methyl group, an aryl group, an alkyl group, an alkylaryl group or an aralkyl group.

The following commercially available ingredients may especially be used as product a):
- Mirasil DM 500000, Rhodia (INCI: Dimethicone),
- Mirasil DME-2, Rhodia (INCI: dimethicone)
- Mirasil DME30, Rhodia (INCI: dimethicone)
- Mirasil ADM-E, Rhodia (INCI: amodimethicone)
- Dow Corning 1784 HVF, Dow Corning (INCI: Dimethiconol)
- Dow Corning 1784 HMW, Dow Corning (INCI: Divinyldimethicone/dimethicone)
- Mirasil DMCP-93, Rhodia (INCI: PEG/PPG-10/2 dimethicone)
- Parsol SLX, DSM (INCI: Polysilicone-15)
- Mirasil SM, Rhodia (INCI: Simethicone)
- Mirasil DMCO, Rhodia (INCI PEG/PPG-22/24 Dimethicone)
- Mirasil DM 100000, Rhodia (INCI: Dimethicone)
- DC200 fluid 60000, Dow Corning (INCI: Dimethicone)
- DC200 fluid 300000, Dow Corning (INCI: Dimethicone).

Polymer for Aiding Deposition b)

The concentrated ingredient comprises at least one polymer for aiding deposition. It is not excluded for it to comprise a mixture or a combination of such polymers. Polymers for aiding deposition that may be used are detailed below.

The polymer for aiding deposition may be chosen especially from:
b1) derivatives of natural polymers comprising cationic or potentially cationic groups, for example cationic cellulose, guar or starch derivatives, and
b2) synthetic polymers comprising cationic or potentially cationic groups, and zwitterionic groups.

The term "potentially anionic units or groups or monomers" means units or groups or monomers whose charge may be neutral or anionic depending on the pH. The term "potentially cationic units or groups or monomers" means units or groups or monomers whose charge may be neutral or cationic depending on the pH. The term "zwitterionic units or groups or monomers" means units simultaneously bearing two charges.

Polymers of Type b1)

For these polymers, the cationic or potentially cationic groups are generally obtained by modifying a polymer. This is often referred to correctly or as abuse of language as a cationization, quaternization, derivatization, functionalization or grafting.

Examples that are mentioned include cationic polysaccharide derivatives, for instance guar or cellulose derivatives. Cationic functionalized polymers, functionalized with hydrophobic or hydrophilic groups, for instance C1-C14 and preferably C2-C8 alkyl chains, optionally containing a hydroxyl group, may be used. These groups are attached to the main polymer chain via ether bonds.

Moreover, and in the case of hydrophobic or non-hydrophobic cationic guars, the cationic group is a quaternary ammonium group bearing three radicals, which may be identical or different, chosen from hydrogen and an alkyl radical containing 1 to 22, more particularly 1 to 14 and advantageously 1 to 3 carbon atoms. The counterion may be a halogen, preferably chlorine.

In the case of hydrophobic or non-hydrophobic modified cationic celluloses, the cationic group is a quaternary ammonium group bearing three radicals, which may be identical or different, chosen from hydrogen and an alkyl radical containing 1 to 10 carbon atoms, more particularly 1 to 6 and advantageously 1 to 3 carbon atoms. The counterion may be halogen, preferably chlorine.

Among the cationic guar derivatives that may be mentioned are guar hydroxypropyl trimonium chloride (Jaguar C13S, C14S, or C17 and Jaguar Excel, sold by the company Rhodia Chimie) or hydroxypropyl guar hydroxypropyl trimonium chloride (Jaguar C162 sold by RHODIA).

Among the cationic cellulose derivatives that may be used are poly(1,2-oxyethanediyl)-2-hydroxy-3-trimethylammonium propyl chloride cellulose ether or polyquaternium-10, or Polymer JR400 (INPI name: PQ10) sold by the company Amerchol.

Nonionic polysaccharide derivatives may also be used, for example hydroxypropyl guar.

The natural cationic polymers more particularly have a weight-average molar mass of at least 2000 g/mol and more preferentially between $2 \times 10^4$ and $3 \times 10^6$ g/mol, depending on their possible degree of polymerization. The weight-average molar masses of the polymers are usually measured by size exclusion. Optionally, they may be measured directly by light scattering or via the intrinsic viscosity using a calibration according to: "Viscosity-Molecular weight relationship, intrinsic chain flexibility and dynamic solution properties of guar galactomannan" by G. Robinson, S. B. Ross Murphy, E. R. Morris, Carbohydrate Research 107, p. 17-32, 1982.

In the case of cationic polysaccharide derivatives, especially guars, the degree of hydroxyalkylation (molar substitution or MS) is preferably between 0 and 1.2. Still in the case of these polymers, the degree of cationicity (degree of substitution or DS) is more particularly between 0.01 and 0.6. This is the case, for example, for Jaguars C162 and C2000 sold by the company Rhodia Chimie.

Polymer of Type b2)

These polymers may be obtained by (co)polymerization of monomers bearing cationic or potentially cationic or zwitterionic groups, or by modification of polymers after polymerization. In the latter case, this is often referred to correctly or as an abuse of language as cationization, quaternization, derivatization, functionalization or grafting. In the present patent application, a monomer-based unit is understood as being a unit as would be obtained directly by polymerization of said monomer. Thus, a unit that would be obtained by polymerization of a monomer followed by modification does not cover the unit derived from the polymerization of the monomer before modification. On the other hand, such a unit covers the unit that would be obtained by a monomer leading after polymerization to a unit that would have the same formula has the modified unit. In the present patent application, the term "copolymer" covers polymers comprising two types of unit, three types of unit (these are occasionally referred to as terpolymers) or more.

The polymer of type b2) may be a (co)polymer, which is preferably statistical, chosen from the following:

(co)polymers comprising:
    cationic or potentially cationic units $B_{CAT}$, and
    optionally, other units chosen from anionic or potentially anionic units $B_A$, nonionic units $B_N$, and zwitterionic units $B_Z$, and combinations thereof, or (co)polymers comprising:
    zwitterionic units $B_Z$, and
    optionally, other units chosen from anionic or potentially anionically units $B_A$, hydrophilic or hydrophobic nonionic units $B_N$, and cationic or potentially cationic units $B_{CAT}$, and combinations thereof.

It is mentioned that copolymers containing both cationic or potentially cationic units $B_{CAT}$ and anionic or potentially anionic units $B_A$ are often referred to as amphoteric or ampholytic copolymers. They are occasionally, incorrectly, referred to as zwitterionic polymers. In the present patent application, a zwitterionic (co)polymer denotes a (co)polymer comprising zwitterionic units $B_Z$ and optionally other units.

As examples of potentially cationic monomers $B_{CAT}$ from which the potentially cationic units $B_{CAT}$ may be derived, mention may be made of:

α,β-monoethylenically unsaturated carboxylic acid N,N (dialkylamino-ω-alkyl)amides, for instance N,N-dimethylaminomethyl-acrylamide or -methacrylamide, 2(N,N-dimethylamino)ethyl-acrylamide or -methacrylamide, 3(N,N-dimethyl-amino)propyl-acrylamide or -methacrylamide and 4(N,N-dimethylamino)butyl-acrylamide or -methacrylamide;

α,β-monoethylenically unsaturated amino esters, for instance 2(dimethylamino)ethyl acrylate (DAEA), 2(dimethylamino)ethyl methacrylate (DAEMA), 3(dimethyl-amino)propyl methacrylate, 2(tert-butylamino)ethyl methacrylate, 2(dipentyl-amino)ethyl methacrylate, or 2(diethylamino)ethyl methacrylate;

vinylpyridines;

vinylamine;

vinylimidazolines;

monomers that are precursors of amine functions such as N-vinylformamide, N-vinylacetamide, etc. which generate primary amine functions by simple acid or basic hydrolysis.

As examples of cationic monomers $B_{CAT}$ from which the units $B_{CAT}$ may be derived, mention may be made of:

ammoniumacryloyl or acryloyloxy monomers, for instance:

trimethylammoniumpropyl methacrylate chloride, trimethylammoniumethylacrylamide or methacrylamide chloride or bromide, trimethylammoniumbutylacrylamide or methacrylamide methyl sulfate, trimethylammoniumpropylmethacrylamide methyl sulfate (TAPMA-MES), (3-methacrylamidopropyl)trimethylammonium chloride (MAPTAC), (3-acrylamidopropyl)trimethylammonium chloride (APTAC), methacryloyloxyethyltrimethylammonium chloride or methyl sulfate (MADAMQUAT CI or MADAMQUAT MeS), acryloyloxyethyltrimethylammonium chloride; or acryloyloxyethyltrimethylammonium methyl sulfate (ADAMQUAT CI or ADAMQUAT MeS), 1-ethyl-2-vinypyridinium or 1-ethyl-4-vinylpyridinium bromide, chloride or methyl sulfate;

N,N-dialkyldiallylamine monomers, for instance N,N-dimethyldiallylammonium chloride (DADMAC);

dimethylaminopropylmethacrylamide-N-(3-chloro-2-hydroxypropyl)trimethylammonium chloride (DIQUAT chloride), dimethylaminopropylmethacrylamide-N-(3-methyl-sulfato-2-hydroxypropyl)trimethylammonium methyl sulfate (DIQUAT methyl sulfate)

the monomer of formula:

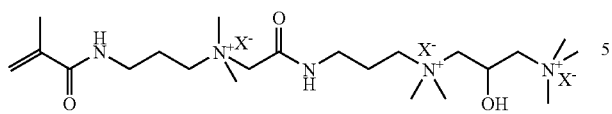

in which X⁻ is an anion, preferably chloride or methyl sulfate.

As examples of hydrophobic nonionic monomers $B_N$ from which the hydrophobic units $B_N$ may be derived, mention may be made of:
- vinylaromatic monomers such as styrene, α-methylstyrene, vinyltoluene, etc.,
- vinyl or vinylidene halides, for instance vinyl chloride or vinylidene chloride,
- $C_1$-$C_{12}$ alkyl esters of α,β-monoethylenically unsaturated acids such as methyl, ethyl or butyl acrylates and methacrylates, 2-ethylhexyl acrylate, etc.,
- vinyl or allylic esters of saturated carboxylic acids such as vinyl or allyl acetates, propionates, versatates, stearates, etc.,
- α,β-monoethylenically unsaturated nitriles containing from 3 to 12 carbon atoms, for instance acrylonitrile, methacrylonitrile, etc.,
- α-olefins, for instance ethylene, etc.,
- conjugated dienes, for instance butadiene, isoprene' soprene or chloroprene.

As examples of hydrophilic nonionic monomers $B_N$ from which the hydrophilic nonionic units $B_N$ may be derived, mention may be made of:
- hydroxyalkyl esters of α,β-ethylenically unsaturated acids, for instance hydroxyethyl or hydroxypropyl acrylates and methacrylates, glyceryl monomethacrylate, etc.,
- α,β-ethylenically unsaturated amides, for instance acrylamide (AM), methacrylamide, N,N-dimethylmethacrylamide, N-methylolacrylamide, etc.,
- α,β-ethylenically unsaturated monomers bearing a water-soluble polyoxyalkylene segment of the polyethylene oxide type, for instance polyethylene oxide α-methacrylates (Bisomer S20W, S10W, etc. from Laporte) or α,ω-dimethacrylates, Sipomer BEM from Rhodia (polyoxyethylene ω-behenyl methacrylate), Sipomer SEM-25 from Rhodia (polyoxyethylene ω-tristyrylphenyl methacrylate), etc.,
- α,β ethylenically unsaturated monomers that are precursors of hydrophilic units or segments such as vinyl acetate, which, one polymerized, may be hydrolyzed to generate vinyl alcohol units or polyvinyl alcohol segments,
- vinylpyrrolidone (VP)
- α,β-ethylenically unsaturated monomers of ureido type and in particular 2-imidazolidinoneethylmethacrylamide (Sipomer WAM II from RHODIA)

As examples of anionic or potentially anionic monomers $B_A$, from which the anionic or potentially anionic units $B_A$ may be derived, mention may be made of:
- monomers containing at least one carboxylic function, for instance α,β-ethylenically unsaturated carboxylic acids or the corresponding anhydrides, such as acrylic, methacrylic or maleic acid or anhydride, fumaric acid, itaconic acid, N-methacroylalanine, or N-acryloylglycine, and the water-soluble salts thereof,
- monomers that are precursors of carboxylate functions, for instance tert-butyl acrylate, which generate, after polymerization, carboxylic functions by hydrolysis,
- monomers containing at least one sulfate or sulfonate function, for instance 2-sulfoxyethyl methacrylate, vinylbenzenesulfonic acid, allylsulfonic acid, 2-acrylamido-2-methylpropanesulfonic acid, sulfoethyl acrylate or methacrylate, and sulfopropyl acrylate or methacrylate, and the water-soluble salts thereof,
- monomers containing at least one phosphonate or phosphate function, for instance vinylphosphonic acid, ethylenically unsaturated phosphate esters such as phosphates derived from hydroxyethyl methacrylate (Empicryl 6835 from Rhodia) and those derived from polyoxyalkylene methacrylates, and the water-soluble salts thereof.

As examples of zwitterionic monomers $B_Z$ from which the zwitterionic units $B_Z$ may be derived, mention may be made of:
- monomers bearing a carboxybetaine group (carboxyalkylammonium in which the alkyl group is optionally substituted with a hydroxyl),
- monomers bearing a pyrridinium carboxyalkyl group in which the alkyl group is optionally substituted with a hydroxyl, and
- monomers bearing an imidazolium carboxyalkyl group in which the alkyl group is optionally substituted with a hydroxyl.

The overall charge of the polymer for aiding deposition is advantageously positive or zero, at the pH of the concentrated ingredient or at the pH of use of the ingredient.

Polymers for aiding deposition that are particularly advantageous are the following (co)polymers:
- cationic copolymers comprising units derived from vinylpyrrolidone and cationic units, preferably copolymers comprising vinylpyrrolidone units, vinylimidazolium units (for example cationized vinylimidazole) or MADAMQUAT units (cationized dimethylaminoethyl methacylate), and optionally units derived from vinylcaprolactam,
- cationic or ampholytic (co)polymers comprising units derived from DADMAC, optionally units derived from acrylic acid, and optionally units derived from acrylamide,
- cationic or ampholytic (co)polymers comprising units derived from MAPTAC, optionally units derived from acrylic acid and optionally units derived from acryalmide,
- copolymers derived from vinylpyrrolidone and from MAPTAC;
- the copolymers described below as "advantageous copolymers".

Cationic or ampholytic polymers that may serve as polymers for aiding deposition are especially polymers of polyquaternium type according to the INCI terminology familiar to those skilled in the art, chosen, for example, from the polymers of Table I below.

TABLE 1

| INCI name | Type | Chemical nature and/or CAS number | Commercial compounds |
|---|---|---|---|
| Polyquaternium-2 | b2 | CAS 63451-27-4 | Mirapol A15, Rhodia |
| Polyquaternium-4 | a1 | CAS 92183-41-0 | Celquat L200, H100, National Starch |
| Polyquaternium-5 | b2 | CAS 26006-22-4 | |
| Polyquaternium-6 | b2 | DADMAC polymer CAS 26062-79-3 | Merquat 1000, Nalco, Mirapol 100, Rhodia |
| Polyquaternium-7 | b2 | Copolymer of DADMAC and of acrymide CAS 26590-05-6 | Merquat 5500, Nalco; Mirapol 550, Rhodia |
| Polyquaternium-10 | a1 | Hydroxyethylcellulose modified with trimethylammoniums | Polymer JR 400, Amercol; Celquat SC230M or SC-240C, National Starch |
| Polyquaternium-11 | b2 | Copolymers of vinylpyrrolidone and of quaternized dimethylaminoethyl methacylate | Gafquat 755N, ISP; Luviquat PQ11PN, BASF |
| Polyquaternium-16 | b2 | CAS 29297-55-0 | Luviquat HM 552, Luviquat FC 370, BASF |
| Polyquaternium-17 | b2 | CAS 90624-75-2 | Mirapol AD1, Rhodia |
| Polyquaternium-19 | b2 | CAS 110736-85-1 | |
| Polyquaternium-22 | b2 | Copolymer of DADMAC and of acrylic acid | Merquat 280, 281, 298, Nalco |
| Polyquaternium-24 | a1 | Hydroxyethylcellulose modified with quaternary ammoniums containing long alkyl chains | Quartisoft LM200, Amercol |
| Polyquaternium-27 | b2 | | Merquat 2001, Nalco |
| Polyquaternium-28 | b2 | Copolymer of vinylpyrrolidone and of MAPTAC | Gatquat HS 100, BASF |
| Polyquaternium-29 | b2 | Chitosan derivative modified with propylene oxide and quaternized with epichlorohydrin | Kytamer KCO, Amerchol, Lexquat CH |
| Polyquaternium-31 | b2 | CAS 136505-02-7 and 139767-67-7 | Hypan HQ |
| Polyquaternium-32 | b2 | CAS 254429-19-7 | |
| Polyquaternium-37 | b2 | CAS 35429-19-7 | |
| Polyquaternium-39 | b2 | | Merquat 3300, 3331, Nalco |
| Polyquaternium-44 | b2 | | Luviquat Care, BASF |
| Polyquaternium-46 | b2 | copolymers of vinylcaprolactam, vinylpyrrolidone, and cationized vinylimidazole | Luviquat Hold, BASF |
| Guar hydroxypropylammonium chloride | a1 | | Jaguar C13S, C14S, C17, Excel, Rhodia |
| Hydroxypropyl guar hydroxypropylammonium chloride | a1 | | Jaguar C162, Rhodia |
| Undergoing validation | a1 | Hydroxyethylcellulose modified with quaternary ammoniums containing long alkyl chains and with short-chain quaternary ammoniums | Softcat SL, Amerchol |
| Polymethacrylamidopropyl-trimonium chloride | | MAPTAC polymer | Polycare 133, Rhodia |
| Acrylamidopropyltrimonium chloride/acrylamide copolymer | | | Salcare SC-60, Ciba |

Advantageous Copolymers

According to one particularly advantageous embodiment, the polymer for aiding deposition is an ampholytic copolymer of type b2) comprising:

0.1% to 50% by number of units $Ei_{CAT}$ derived from the polymerization of at least one monomer compound $B_{CAT}$ of general formula I:

$$H_2C=\overset{R1}{\underset{|}{C}}-Z-[CH_2]_n-\overset{R2}{\underset{R3}{\overset{|}{N^+}}}-[A-\overset{R2}{\underset{R3}{\overset{|}{N^+}}}-]_m B-\overset{R4}{\underset{R6}{\overset{|}{N^+}}}-R5 \quad X^-\ X^-\ X^-$$

in which:
  $R_1$ is a hydrogen atom or a methyl or ethyl group;
  $R_2$, $R_3$, $R_4$, $R_5$ and $R_6$, which may be identical or different, are linear or branched $C_1$-$C_6$ and preferably $C_1$-$C_4$ alkyl, hydroxyalkyl or aminoalkyl groups,
  m is an integer from 0 to 10 and preferably from 0 to 2;
  n is an integer from 1 to 6 and preferably from 2 to 4;
  Z represents a —C(O)O— or —C(O)NH— group or an oxygen atom;
  A represents a group $(CH_2)_p$, p being an integer from 1 to 6 and preferably from 2 to 4;
  B represents a linear or branched $C_2$-$C_{12}$ and advantageously $C_3$-$C_6$ polymethylene chain, optionally interrupted with one or more heteroatoms or hetero groups, especially O or NH, and optionally substituted with one or more hydroxyl or amino groups, preferably hydroxyl groups;
  $X^-$, which may be identical or different, represent counterions;

units $B_A$ derived from the polymerization of at least one hydrophilic monomer $B_A$ bearing a function of acidic nature that is copolymerizable with $B_A$, which is anionic or potentially anionic, optionally units $B_N$ derived from at least one ethylenically unsaturated monomer $B_N$ of neutral charge, which is copolymerizable with $B_{CAT}$ and $B_A$, preferably an ethylenically unsaturated hydrophilic monomer copolymer of neutral charge bearing one or more hydrophilic groups, which is copolymerizable with $B_{CAT}$ and $B_A$, the amount of units $B_A$ and optionally $B_N$ being from 50% to 99.9% by number.

The ion $X^-$ is advantageously chosen from halide, for example chloride, sulfate, methyl sulfate, hydrosulfate, phosphate, citrate, formate and acetate.

The copolymer advantageously has a molecular mass of at least 1000 and advantageously of at least 10 000; it may be up to 20 000 000 and advantageously up to 10 000 000. It is preferably between 500 000 and 5 000 000. Unless otherwise mentioned, when the term molecular mass is used, it will be the weight-average molecular mass, expressed in g/mol. This may be determined by aqueous gel permeation chromatography (GPC) or by measurement of the intrinsic viscosity in a 1N solution of $NaNO_3$ at 30° C.

The copolymer is preferably a random copolymer.

Preferably, in the general formula (I) of the monomer $B_{CAT}$,
  Z represents C(O)O, C(O)NH or O, and most preferably C(O)NH;
  n is equal to 2 or 3 and most particularly 3 m ranges from 0 to 2, it is preferably equal to 0 or 1 and most particularly 0;
  B represents:

$$-CH_2-\overset{OH}{\underset{|}{CH}}-(CH_2)_q$$

with q from 1 to 4, preferably equal to 1;
  $R_1$ to $R_6$, which may be identical or different, represent a methyl or ethyl group.

The preferred monomer (c) is the DIQUAT having the following formula:

$$H_2C=\overset{CH_3}{\underset{|}{C}}-\overset{O}{\underset{}{C}}-NH-[CH_2]_3-\overset{CH_3}{\underset{CH_3}{\overset{|}{N^+}}}-CH_2-\overset{OH}{\underset{|}{CH}}-CH_2-\overset{CH_3}{\underset{CH_3}{\overset{|}{N^+}}}-CH_3 \quad X^-\ X^-$$

$X^-$ representing a chloride or methyl sulfate ion.

Other monomers (c) that are particularly advantageous are:

$$H_2C=\overset{CH_3}{\underset{|}{C}}-\overset{O}{\underset{}{C}}-NH-[CH_2]_3-\overset{CH_3}{\underset{CH_3}{\overset{|}{N^+}}}-[CH_2]_p-\overset{CH_3}{\underset{CH_3}{\overset{|}{N^+}}}-CH_2-\overset{OH}{\underset{|}{CH}}-CH_2-\overset{CH_3}{\underset{CH_3}{\overset{|}{N^+}}}-CH_3 \quad X^-\ X^-\ X^-$$

in which p=2 to 4.

The anions $X^-$ are especially a halogen anion, preferably a chloride, sulfonate, sulfate, methyl sulfate, hydrogen sulfate, phosphate, phosphonate, citrate, formate or acetate anion.

The monomers $B_A$ are advantageously monoethylenically unsaturated $C_3$-$C_8$ carboxylic, sulfonic, sulfuric, phosphonic or phosphoric acids, anhydrides thereof and water-soluble salts thereof.

Among the preferred monomers $B_A$ that may be mentioned are acrylic acid, methacrylic acid, α-ethacrylic acid, β,β-dimethylacrylic acid, methylenemalonic acid, vinylacetic acid, allylacetic acid, ethylidineacetic acid, propylidineacetic acid, crotonic acid, maleic acid, fumaric acid, itaconic acid, citraconic acid, mesaconic acid, N-methacryloylalanine, N-acryloylhydroxyglycine, sulfopropyl acrylate, sulfoethyl acrylate, sulfoethyl methacrylate, sulfoethyl methacrylate, styrenesulfonic acid, vinylsulfonic acid, vinylphosphonic acid, phosphoethyl acrylate, phosphonoethyl acrylate, phosphopropyl acrylate, phosphonopropyl acrylate, phosphoethyl methacrylate, phosphonoethyl methacrylate, phosphopropyl methacrylate and phosphonopropyl methacrylate, and the alkali metal and ammonium salts thereof.

Among the monomers $B_N$ that may be mentioned are acrylamide, vinyl alcohol, $C_1$-$C_4$ alkyl esters of acrylic acid and of methacrylic acid, $C_1$-$C_4$ hydroxyalkyl esters of acrylic acid and of methacrylic acid, especially ethylene glycol and propylene glycol acrylate and methacrylate, polyalkoxylated esters of acrylic acid and of methacrylic acid, especially the polyethylene glycol and polypropylene glycol esters, esters of acrylic acid or of methacrylic acid and of polyethylene glycol or polypropylene glycol mono($C_1$-$C_{25}$)alkyl ethers, vinyl acetate, vinylpyrrolidone and methyl vinyl ether.

The copolymer comprises from 0.1% to 50% by number of units $B_{CAT}$ and from 50% to 99.1% by number of units $B_A$ and optionally $B_N$. Preferably, the polymer comprises from 10% to 40% of units $B_{CAT}$ and from 60% to 90% of units $B_A$ and optionally $B_N$. Moreover, the polymer advantageously does not comprise any units $B_N$. If the copolymer does comprise units $B_N$, the molar ratio between the units $B_A$ and the units $B_N$ is preferably greater than 1, for example between 1 and 4.

Preferably, the polymer is such that
the units $B_{CAT}$ are derived from a monomer $B_{CAT}$ of the following formula:

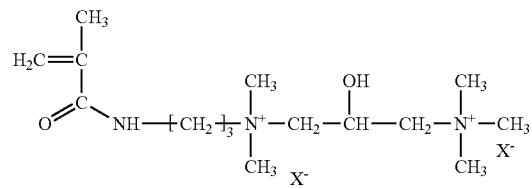 [SMILES: C=C(C)C(=O)NC[N+](C)(C)CC(O)C[N+](C)(C)C]

$X^-$ representing a chloride or methyl sulfate ion,
the units $B_A$ are derived from acrylic acid,
the polymer does not comprise any units $B_N$,
the numerical ratio between the units $B_A$ and the units $B_{CAT}$ is from 50/50 to 90/10.

It is pointed out that the copolymers may have a mean positive, negative or zero charge, at the pH of the concentrated ingredient or at the pH of use of the concentrated ingredient. This mean charge is defined by the following equation:

$$Q = \frac{[c]X_c - [a]X_a}{[c]X_c + [a]X_a}$$

in which:
[c] is the molar concentration of units $B_{CAT}$,
[a] is the molar concentration of units $B_A$,
$X_C$ represents the possible degree of neutralization of the units $B_{CAT}$ (in the case where the units $B_{CAT}$ are potentially cationic); $X_C=[BH^+]/([B]+[BH^+])$,
$X_A$ represents the possible degree of neutralization of the units $B_A$ (in the case where the units $B_A$ are potentially anionic); $X_A=[A^-]/([AH]+[A^-])$.

One copolymer that is particularly preferred is the following:

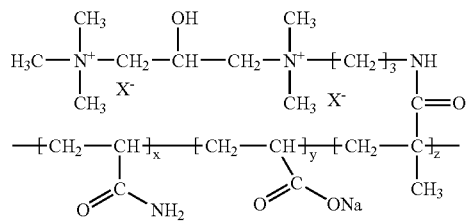

with
x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1,
x+y is from 50% to 99.9%,
x+y+z=100%, x, y and z representing the molar percentages of units derived, respectively, from acrylamide, acrylic acid (sodium salt) and DIQUAT.

Other polymers are as follows:

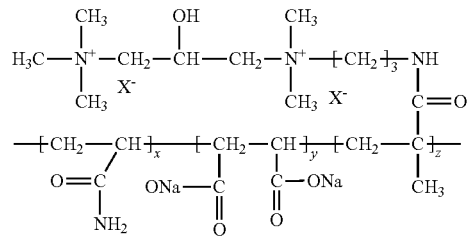

x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1,
x+y is from 50% to 99.9%.

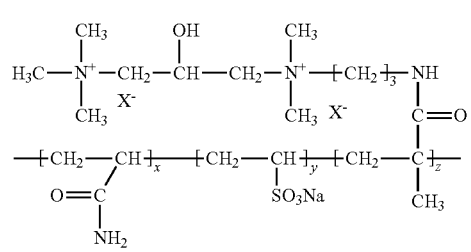

x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1,
x+y is from 50% to 99.9%.

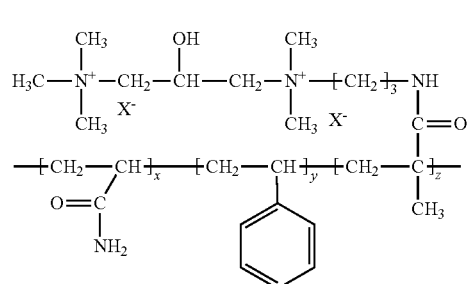

x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1,
x+y is from 50% to 99.9%.

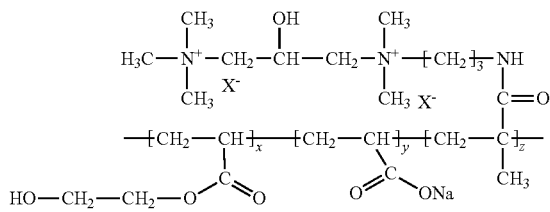

x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1,
x+y is from 50% to 99.9%.

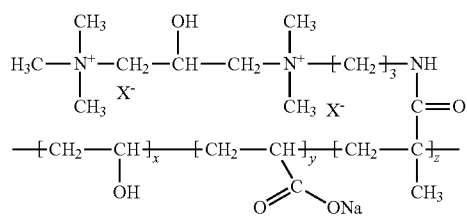

x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1
x+y is from 50% to 99.9%.

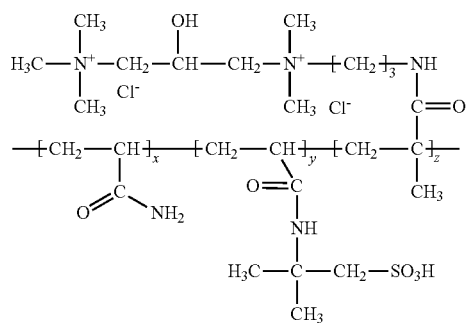

x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1,
x+y is from 50% to 99.9%.

Surfactant c)

Useful surfactants that may especially serve for the emulsification for the preparation of a polyorganosiloxane emulsion are especially nonionic surfactants, which are preferably polyalkoxylated, chosen, for example, from alkoxylated fatty alcohols, alkoxylated triglycerides, alkoxylated fatty acids, alkoxylated sorbitan esters, alkoxylated fatty amines, alkoxylated bis(1-phenylethyl)phenols, alkoxylated tris(1-phenylethyl)phenols and alkoxylated alkylphenols, in which the number of alkoxyl units, more particularly oxyethylene and/or oxypropylene, is such that the HLB value is greater than or equal to 10.

However, it is also possible to use other surfactants, especially those mentioned below for the cosmetic compositions.

Use of the Ingredient and Cosmetic Composition

The concentrated ingredient may be used in a cosmetic composition. The composition may be prepared by mixing the concentrated ingredient, prepared beforehand, with other ingredients.

The cosmetic composition thus generally comprises:
a cosmetically acceptable vector, for example an aqueous, alcoholic or aqueous-alcoholic vector,
optionally at least one surfactant, and
the ingredient according to the invention, itself comprising the conditioning agent and the polymer for aiding deposition.

In the cosmetic composition, the conditioning agent is advantageously present in a physical form identical to that of the concentrated ingredient, for example in the form of an emulsion preferably with a substantially identical droplet size. The, physical form may depend on the other ingredients of the composition and on the process for preparing said composition. High shears may lead, for example, to smaller droplet sizes.

Needless to say, the cosmetic composition may comprise other ingredients. It may especially comprise other conditioning agents and/or other polymers for aiding deposition, which may be chosen from those mentioned above.

The weight proportion of surfactant in the composition is between 0 and 30% and preferably between 5% and 30% by weight. The surfactant comprises an anionic, cationic, nonionic or amphoteric surfactant, or a mixture of these surfactants, preferably an anionic surfactant optionally with an amphoteric surfactant.

The weight proportion of the polymer for aiding deposition in the composition is preferably between 0.01% and 5%, preferably between 0.05% and 1.5% and preferably from 0.1% to 0.3% (as active material).

The weight proportion of the conditioning agent in the composition may especially be greater than 1%, for example between 1% and 10%.

The compositions are preferably compositions intended to be rinsed out. Such a composition may be, for example, a shampoo, a shower gel or a hair conditioner.

However, it may be a haircare composition that is not intended to be rinsed out, for example a hair conditioner not intended to be rinsed out, a disentangling milk, a disentangling lotion, a smoothing lotion, a cuticle coating, a styling and/or restyling haircare product, an antisun product, a care cream, a makeup remover, a makeup, makeup-removing or moisturizing wipes, shaving foams and styling or fixing foams.

Cosmetically Acceptable Vector

This is a topical application vector for the skin and/or the hair.

Any cosmetically acceptable vector allowing the ampholytic polymer to be formulated and making it possible to obtain the desired cosmetic composition form, for the intended use, may be used. Various cosmetically acceptable vectors for different types of formulation are known to those skilled in the art.

Examples of cosmetically acceptable vectors that may be mentioned include aqueous vectors (comprising water), alcoholic vectors (comprising an alcohol, for example ethanol, isopropanol, ethylene glycol or polyethylene glycols), propylene glycol, aqueous-alcoholic vectors (comprising a mixture of water and of an alcohol, for example ethanol, isopropanol, ethylene glycol or polyethylene glycols). Certain volatile or nonvolatile oils may also be used. Mention may be made, for example, of fluid silicones, such as cyclopentasiloxane, for example Mirasil CM5 sold by Rhodia.

A person skilled in the art knows how to select the vectors that are suitable for the desired types of formulation, and for the intended uses. For example aqueous vectors are generally used for shampoos or shower gels. A propylene glycol vector may be used for compositions in the form of creams. A cyclomethicone vector may be used for makeup compositions, for example for foundations.

Surfactants of the Cosmetic Composition

The composition is a generally aqueous composition optionally comprising surfactants. It may be a mixture of different surfactants. The surfactants included in the composition preferably comprise at least one anionic surfactant. The surfactants may also comprise amphoteric surfactants (true amphoteric or zwitterionic surfactants), neutral surfactants (nonionic surfactants) and/or cationic surfactants. The compositions comprising at least one anionic surfactant and at least one amphoteric surfactant are particularly advantageous, especially for reasons of softness. The total amount of surfactants in the composition is between 0 and 30% by weight.

For compositions intended for treating the hair, for instance shampoos, the surfactant content is advantageously between 10% and 20% by weight. Such compositions may comprise salts, for example sodium or ammonium chloride, advantageously in a content of less than 3% by weight.

For compositions intended for treating the skin, for instance shower gels, the surfactant content is advantageously between 5% and 15% by weight. Such compositions also preferably comprise at least 2% by weight of salts, for example sodium or ammonium chloride.

The weight proportion of anionic surfactants relative to the total amount of surfactants is preferably greater than 50% and preferentially greater than 70%.

For hair conditioners, the surfactant content may be less than 5% by weight. They may preferably be cationic surfactants.

Parameters (pH)

The pH of the composition generally depends on its intended purpose and its use. The pH is generally between 3.5 and 7.7. It is preferably greater than or equal to 4.5 and more preferably 5.5. It is, for example, between 5.5 and 7.5 and preferably between 6 and 6.5. The pH obviously depends on the compounds present in the composition. Acidic or basic pH regulators, for example citric acid, or sodium hydroxide, potassium hydroxide or ammonium hydroxide, may obviously be used in the composition. For compositions intended for haircare, especially for leave-in hair conditioners, which may especially comprise cationic surfactants, generally in small amounts (less than 5% by weight), the pH may be relatively acidic, for example from 3.5 to 5.5.

Nature of the Surfactants of the Cosmetic Composition

The anionic surfactants may be chosen from the following surfactants:

alkyl ester sulfonates, for example of formula R—CH($SO_3M$)-$CH_2COOR'$, or alkyl ester sulfates, for example of formula R—CH($OSO_3M$)-$CH_2COOR'$, in which R represents a $C_9$-$C_{20}$ and preferably $C_{10}$-$C_{16}$ alkyl radical, R' a $C_1$-$C_6$ and preferably $C_1$-$C_3$ alkyl radical and M an alkaline-earth metal cation, for example sodium, or an ammonium cation. Mention may be made most particularly of methyl ester sulfonates whose radical R is of $C_{14}$-$C_{16}$;

alkylbenzenesulfonates, more particularly of $C_9$-$C_{20}$, primary or secondary alkylsulfonates, especially of $C_8$-$C_{22}$, and alkylglyceryl sulfonates;

alkyl sulfates, for example of formula $ROSO_3M$, in which R represents a $C_{10}$-$C_{24}$ and preferably $C_{12}$-$C_{20}$ alkyl or hydroxyalkyl radical; M represents a cation of the same definition as above;

alkyl ether sulfates, for example of formula $RO(OA)_nSO_3M$ in which R represents a $C_{10}$-$C_{24}$ and preferably $C_{12}$-$C_{20}$ alkyl or hydroxyalkyl radical; OA representing an ethoxylated and/or propoxylated group; M representing a cation of the same definition as above, n generally ranging from 1 to 4, for instance lauryl ether sulfate with n=2;

alkylamide sulfates, for example of formula $RCONHR'OSO_3M$ in which R represents a $C_2$-$C_{22}$ and preferably $C_6$-$C_{20}$ alkyl radical, R' represents a $C_2$-$C_3$ alkyl radical, M representing a cation of the same definition as above, and also the polyalkoxylated (ethoxylated and/or propoxylated) derivatives thereof (alkylamido ether sulfates)

saturated or unsaturated fatty acid salts, for example those of $C_8$-$C_{24}$ and preferably of $C_{14}$-$C_{20}$ and of an alkaline-earth metal cation, N-acyl N-alkyltaurates, alkylisethionates, alkylsuccinamates and alkylsulfosuccinates, sulfosuccinate monoesters or diesters, N-acyl sarcosinates and polyethoxycarboxylates;

phosphate monoesters and diesters, for example having the following formula: $(RO)_x$—P(=O)$(OM)_{x'}$ in which R represents an alkyl, alkylaryl, arylalkyl or aryl radical, which are optionally polyalkoxylated, x and x' being equal to 1 or 2, on condition that the sum of x and x' is equal to 3, M representing an alkaline-earth metal cation.

The nonionic surfactants may be chosen from the following surfactants:

alkoxylated fatty alcohols alkoxylated triglycerides alkoxylated fatty acids alkoxylated sorbitan esters alkoxylated fatty amines alkoxylated bis(1-phenylethyl)phenols alkoxylated tris(1-phenylethyl)phenols alkoxylated alkylphenols products resulting from the condensation of ethylene oxide with a hydrophobic compound resulting from the condensation of propylene oxide with propylene glycol, such as the Pluronic products sold by BASF;

products resulting from the condensation of ethylene oxide with the compound resulting from the condensation of propylene oxide with ethylenediamine, such as the Tetronic products sold by BASF;

alkylpolyglycosides, for instance those described in U.S. Pat. No. 4,565,647;

fatty acid amides, for example of $C_8$-$C_{20}$.

The amphoteric surfactants (true amphoteric surfactants comprising an ionic group and a potentially ionic group of opposite charge, or zwitterionic surfactants simultaneously comprising two opposite charges) may be chosen from the following surfactants:

betaines in general, especially carboxy betaines, for example lauryl betaine (Mirataine BB from the company Rhodia) or octyl betaine; amidoalkyl betaines, for instance cocamidopropyl betaine (CAPB) (Mirataine BDJ from the company Rhodia Chimie);

sulfobetaines or sultaines, for instance cocamidopropyl hydroxy sultaine (Mirataine CBS from the company Rhodia);

alkylamphoacetates and alkylamphodiacetates, for instance those comprising a coco or lauryl chain (Miranol C2M, C32 and L32 especially, from the company Rhodia);

alkylamphopropionates or alkylamphodipropionates, (Miranol C2M SF);

alkyl amphohydroxypropyl sultaines (Miranol CS).

The cationic surfactants may be chosen from primary, secondary or tertiary, optionally polyethoxylated fatty amine salts, quaternary ammonium salts such as tetraalkylammonium, alkylamidoalkylammonium, trialkylbenzylammonium, trialkyl-hydroxyalkylammonium or alkylpyridinium chlorides or bromides, imidazoline derivatives and amine oxides of cationic nature.

Examples of useful compositions that may be mentioned include:

the "sodium" compositions for shampoos typically comprising 12% to 16% by weight of sodium alkyl ether sulfate (for example sodium lauryl ether sulfate "SLES") or a mixture of sodium alkyl ether sulfate and of sodium alkyl sulfate (for example sodium lauryl sulfate "SLS"), 1% to 3% of an amphoteric surfactant (for example cocoamidopropyl betaine "CAPB"), 0.5% to 2% of a salt (for example sodium chloride);

the "ammonium" compositions for shampoos typically comprising 12% to 16% by weight of ammonium alkyl ether sulfate (for example ammonium lauryl ether sulfate "ALES") or of a mixture of ammonium alkyl ether sulfate and of ammonium alkyl sulfate (for example ammonium lauryl sulfate "ALS"), 1% to 3% of an amphoteric surfactant (for example cocoamidopropyl betaine "CAPB"), 0 to 2% of a salt (for example ammonium chloride);

the "sodium" compositions for shower gels typically comprising 6% to 10% by weight of sodium alkyl ether sulfate (for example sodium lauryl ether sulfate "SLES") or a mixture of sodium alkyl ether sulfate and of sodium alkyl sulfate (for example sodium lauryl sulfate "SLS"), 1% to 3% of an amphoteric surfactant (for example cocoamidopropyl betaine "CAPB"), 2% to 4% of a salt (for example sodium chloride);

the "ammonium" compositions for shower gels typically comprising 6% to 10% by weight of ammonium alkyl ether sulfate (for example ammonium lauryl ether sulfate "ALES") or a mixture of ammonium alkyl ether sulfate and of ammonium alkyl sulfate (for example ammonium lauryl sulfate "ALS"), 1% to 3% of an amphoteric surfactant (for example cocoamidopropyl betaine "CAPB"), 0 to 4% of a salt (for example ammonium chloride).

Other Compounds

The composition may comprise any other compound used in cosmetic compositions intended to be rinsed out (shampoo, shower gel, conditioner, etc.) or not intended to be rinsed out. It is not excluded for certain compounds to exert several functions. Such compounds may appear in several sections of the present patent application.

Examples that may be mentioned include sequestering agents, softeners, foam modifiers, colorants, nacreous agents (pearlizers), moisturizers, antidandruff or antiseborrheic agents, suspension agents, emulsifiers, ceramides, pseudoceramides, electrolytes, fatty acids, fatty acid esters, hydroxy acids, thickeners, fragrances, preserving agents, organic or mineral sunscreens, proteins and derivatives thereof, vitamins, stabilizers and rheology modifiers. Some of these compounds are detailed below.

Stabilizers

The composition may advantageously comprise at least one stabilizer. These are also occasionally referred to as suspension agents. It is not excluded for the polymer for aiding deposition also to exert a stabilizing function.

The weight proportion of such agents may typically be from 0.1% to 10% by weight and preferably from 0.3% to 8% by weight for polysaccharides or other agents.

As examples of stabilizers that are particularly useful for compositions comprising polyorganosiloxanes, mention may be made of:

crosslinked polyacrylates, for example polymers of Carbopol or Carbomer type sold by BF Goodrich or Noveon, Acritamer sold by Rita or Tego Carbomer sold by Goldschmidt. These compounds may be typically present in an amount of from 0.1% to 3% and preferably from 0.3% to 2% by weight relative to the composition. Mention is made in particular of crosslinked copolymers of methacrylic acid and of a $C_1$-$C_4$ alkyl acrylate, such as the carbopol Aqua-SF1 from Noveon. Commercial compounds that are mentioned include: Carbopol ETD-2020 from Noveon, Carbopol 980 from Noveon, Carbomer C from Rhodia;

the acrylate/aminoacrylate/PEG-20 $C_{10}$-$C_{30}$ alkyl itaconate copolymers sold by National Starch under the name Structure Plus. These compounds may typically be present in an amount of from 0.1% to 3% and preferably from 0.3% to 2% by weight relative to the composition;

insoluble solids forming a network in the composition. These may be fatty acid monoesters and/or diesters of ethylene glycol, the fatty acids preferably being of $C_{16}$-$C_{18}$. It may be in particular ethylene glycol distearate (EGDS), for example sold by Rhodia as a concentrate with other ingredients under the name Mirasheen. This compound may typically be present in an amount of from 3% to 10% and preferably from 5% to 8% by weight relative to the composition. Such a compound may be introduced into the composition via any known method, especially by cold mixing, where appropriate in crystalline form, or by hot mixing, where appropriate with subsequent crystallization. It may be introduced in the form of a mixture with other compounds, especially surfactants. Mention may be made especially of distearyl ether, ethylene glycol distearate (EGDS) (INCI: glycol distearate), polyethoxylated and/or polypropoxylated stearates and/or distearates, for example PEG-3 distearates, PEG/PPG distearates, PEG-200 distearates or PEG-100 stearates. Commercial products that may be used are especially Mirasheen CP 820, Rhodia; Euperlan PK-3000 AM, Cognis; Euperlan PK-771 BENZ, Cognis; Genapol TS, Clariant (INCI: PEG-3 distearate).

Mention may also be made of viscosifiers, gelling agents or texturing agents, for instance anionic acrylic copolymers of Aculyne type sold by ISP or Rohm & Haas, for example Aculyne 22, polysaccharides and the noncationic derivatives thereof, such as cellulose derivatives, for instance hydroxypropylcellulose, carboxymethylcellulose, nonionic guar derivatives, for instance hydroxypropyl guar (for example the Jaguar HP products sold by Rhodia), locust bean gum, tara gum or cassia gum, xanthan gum (for example the Rhodicare products sold by Rhodia), succinoglycans (for example Rheozan sold by Rhodia), alginates, carrageenans, chitin derivatives or any other polysaccharide with a texturing function. These polysaccharides and derivatives thereof may be incorporated alone or in synergistic combination with other polysaccharides. These compounds may typically be present in an amount of from 0.1% to 3% and preferably from 0.3% to 1% by weight relative to the composition.

Other Ingredients of the Cosmetic Composition

Bactericidal or fungicidal agents may also be incorporated into the cosmetic composition, in the form of dispersions or solutions, in order to improve the skin disinfection, for instance triclosan; antidandruff agents, especially such as zinc pyrithione or octopyrox; insecticidal agents, for instance natural or synthetic pyrethroids.

The cosmetic compositions may also contain agents for protecting the skin and/or the hair against attack from sunlight and UV rays. Thus, the compositions may comprise sunsceens, which are chemical compounds that strongly absorb UV radiation, for instance the compounds permitted in European directive No. 76/768/EEC, its appendices and the subsequent modifications of this directive.

When the various components constituting the cosmetic composition are of excessively low solubility in the composition or when they are in solid form at room temperature, said constitutive components may advantageously be dissolved in an organic vehicle, for instance in mineral or natural oils, silicone derivatives or waxes, or alternatively may be encapsulated in matrices, for instance polymers of latex type.

The cosmetic compositions forming the subject of the invention may also contain fixative resins.

When they are present, these fixative resins are generally present in concentrations of between 0.01% and 10% and preferably between 0.5% and 5%.

The fixative resins included in the cosmetic compositions are more particularly chosen from the following resins:

methyl acrylate/acrylamide copolymers, polyvinyl methyl ether/maleic anhydride copolymers, vinyl acetate/crotonic acid copolymers, octylacrylamide/methyl acrylate/butylaminoethyl methacrylate copolymers, polyvinylpyrrolidones, polyvinylpyrrolidone/methyl methacrylate copolymers, polyvinylpyrrolidone/vinyl acetate copolymers, polyvinyl alcohols, polyvinyl alcohol/crotonic acid copolymers, polyvinyl alcohol/maleic anhydride copolymers, hydroxypropylcelluloses, hydroxypropyl guars, sodium polystyrenesulfonates, polyvinylpyrrolidone/ethyl methacrylate/methacrylic acid terpolymers, poly(methyl vinyl ether/maleic acid) monomethyl ethers, polyvinyl acetates grafted onto polyoxyethylene trunks (EP-A-219 048), copolyesters derived from a terephthalic and/or isophthalic and/or sulfoisophthalic acid, anhydride or diester and from a diol, such as:

polyester copolymers based on ethylene terephthalate and/or propylene terephthalate and polyoxyethylene terephthalate units (U.S. Pat. No. 3,959,230, U.S. Pat. No. 3,893,929, U.S. Pat. No. 4,116,896, U.S. Pat. No. 4,702,857, U.S. Pat. No. 4,770,666);

sulfonated polyester oligomers obtained by sulfonation of an oligomer derived from ethoxylated allylic alcohol, dimethyl terephthalate and 1,2-propylene diol (U.S. Pat. No. 4,968,451);

polyester copolymers derived from dimethyl terephthalate, isophthalic acid, dimethyl sulfoisophthalate and ethylene glycol (EP-A-540 374);

copolymers comprising polyester units derived from dimethyl terephthalate, isophthalic acid, dimethyl sulfoisophthalate and ethylene glycol and from polyorganosiloxane units (FR-A-2 728 915);

sulfonated polyester oligomers obtained by condensation of isophthalic acid, dimethyl sulfosuccinate and diethylene glycol (FR-A-2 236 926);

polyester copolymers based on propylene terephthalate and polyoxyethylene terephthalate units and ending with methyl or ethyl units (U.S. Pat. No. 4,711,730) or polyester oligomers ending with alkylpolyethoxy groups (U.S. Pat. No. 4,702,857) or sulfopolyethoxy anionic groups (U.S. Pat. No. 4,721,580), and sulfoaroyls (U.S. Pat. No. 4,877,896);

polyester-polyurethanes obtained by reacting a polyester obtained from adipic acid and/or terephthalic acid and/or sulfoisophthalic acid and from a diol, with a prepolymer containing isocyanate end groups obtained from a polyoxyethylene glycol and from a diisocyanate (FR-A-2 334 698);

ethoxylated monoamines or polyamines, and ethoxylated amine polymers (U.S. Pat. No. 4,597,898, EP-A-11 984).

Preferably, the fixative resins are chosen from polyvinylpyrrolidone (PVP), copolymers of polyvinylpyrrolidone and of methyl methacrylate, copolymer of polyvinylpyrrolidone and of vinyl acetate (VA), polyethylene glycol terephthalate/polyethylene glycol copolymers, polyethylene glycol terephthalate/polyethylene glycol/sodium polyisophthalate sulfonate copolymers, and mixtures thereof.

These fixative resins are preferably dispersed or dissolved in the chosen vehicle.

The cosmetic compositions may also contain polymer derivatives having a protective function.

These polymer derivatives may be present in amounts from about 0.01-10%, preferably about 0.1-5% and most particularly about 0.2-3% by weight.

These agents may be chosen especially from:

nonionic cellulose-based derivatives such as cellulose hydroxy ethers, methylcellulose, ethylcellulose, hydroxypropylmethylcellulose and hydroxybutylmethylcellulose;

polyvinyl esters grafted onto polyalkylene trunks, such as polyvinyl acetates grafted onto polyoxyethylene trunks (EP-A-219 048);

polyvinyl alcohols.

The cosmetic compositions forming the subject of the invention may also comprise plasticizers.

Said plasticizers, when they are present, may represent between 0.1% and 20% and preferably from 1% to 15% of the formulation.

Among the plasticizers that are particularly useful, mention may be made of adipates, phthalates, isophthalates, azelates, stearates, silicone copolyols, glycols and castor oil, or mixtures thereof.

Metal-sequestering agents, more particularly those that sequester calcium, for instance citrate ions, may also advantageously be added to these compositions.

Humectants may also be incorporated into the cosmetic compositions forming the subject of the invention, among which are, inter alia, glycerol, sorbitol, urea, collagen, gelatin, aloe vera, hyaluronic acid or volatile water-soluble solvents, for instance ethanol or propylene glycol, the contents of which may be up to 60% by weight of the composition.

To further reduce the irritation or attack of the scalp, water-soluble or water-dispersible polymers may also be added, for instance collagen or certain non-allergenic derivatives of animal or plant proteins (for example wheat protein hydrolyzates), natural hydrocolloids (guar gum, locust bean gum, tara gum, etc.) or hydrocolloids derived from fermentation processes, and derivatives of these polycarbohydrates, for instance modified nonionic celluloses, for instance hydroxyethylcellulose, or modified anionic celluloses, for instance carboxymethylcellulose; guar derivatives or locust bean gum derivatives, for instance the nonionic derivatives thereof (for example hydroxypropyl guar) or the anionic derivatives thereof (carboxymethyl guar and carboxymethylhydroxypropyl guar).

Mineral powders or particles, for instance calcium carbonate, sodium bicarbonate, calcium dihydrogen phosphate, mineral oxides in powder form or in colloidal form (particles less than about 1 micrometer in size, occasionally a few tens of nanometers), for instance titanium dioxide, silica, aluminum salts generally used as antiperspirants, kaolin, talc, clays and derivatives thereof, etc., may be added in combination to these compounds.

Preserving agents, for instance methyl, ethyl, propyl and butyl esters of p-hydroxybenzoic acid, sodium benzoate, Germaben® or any chemical agent for preventing the proliferation of bacteria or molds that is conventionally used in cosmetic compositions may also be introduced into the aqueous cosmetic compositions according to the invention, generally to a proportion of from 0.01% to 3% by weight.

The amount of these products is usually adjusted to prevent any proliferation of bacteria, molds or yeasts in the cosmetic compositions.

As an alternative to these chemical agents, it may occasionally be possible to use agents that modify the water activity and that greatly increase the osmotic pressure, for instance carbohydrates or salts.

To protect the skin and/or the hair against attack from sunlight and UV rays, organic or mineral sunscreens may be added to the compositions, for example mineral particles, for instance zinc oxide, titanium dioxide or cerium oxides, in powder form or in the form of colloidal particles, alone or as a mixture. These powders may optionally be surface-treated to increase the efficacy of their anti-UV action or to facilitate their incorporation into the cosmetic formulations, or to prevent surface photoreactivity. The organic sunscreens may especially be introduced into the polyorganosiloxane, if it is present in the composition.

One or more fragrances, colorants chosen from, among which mention may be made of the products described in appendix IV ("List of coloring agents allowed for use in cosmetic products") of European directive No. 76/768/EEC of 27 Jul. 1976, known as the Cosmetic Directive, and/or opacifiers, for instance pigments, may be added to these ingredients, if necessary, with the aim of increasing the comfort during the use of the composition by the consumer.

Although this is not obligatory, the composition may also contain viscosifying or gelling polymers so as to adjust the texture of the composition, for instance the crosslinked polyacrylates (Carbopol sold by Goodrich) already mentioned above, noncationic cellulose derivatives, for instance hydroxypropylcellulose or carboxymethylcellulose, guars and nonionic derivatives thereof, xanthan gum and its derivatives, used alone or in combination, or the same compounds, generally in the form of water-soluble polymers modified with hydrophobic groups covalently bonded to the polymer skeleton, as described in patent WO 92/16187 and/or water to bring the total of the constituents of the formulation to 100%.

The cosmetic compositions forming the subject of the invention may also contain polymeric dispersants in an amount of about 0.1-7% by weight, to control the calcium and magnesium hardness, these being agents such as:

water-soluble polycarboxylic acid salts with a weight-average molecular mass of about from 2000 to 100 000 g/mol, obtained by polymerization or copolymerization of ethylenically unsaturated carboxylic acids such as acrylic acid, maleic acid or anhydride, fumaric acid, itaconic acid, aconitic acid, mesaconic acid, citraconic acid or methylenemalonic acid, and most particularly polyacrylates with a weight-average molecular mass of about from 2000 to 10 000 g/mol (U.S. Pat. No. 3,308,067), copolymers of acrylic acid and of maleic anhydride with a weight-average molecular mass of about from 5000 to 75 000 g/mol (EP-A-66 915);

polyethylene glycols with a weight-average molecular mass of about from 1000 to 50 000 g/mol.

Other details or advantages of the invention will emerge more clearly in the light of the examples that follow, which are given without any limiting nature.

EXAMPLES

The following products are especially used to perform Examples 1 to 6:

| Product | Type | Compound |
| --- | --- | --- |
| SLES | Anionic surfactant | sodium lauryl ether sulfate (2EO), EMPICOL ESB/3M sold by Huntsman |
| CAPB | Amphoteric surfactant | Cocoamidopropylbetaine, MirataineBET-C-30 sold by Rhodia |
| Salt | | Sodium chloride or ammonium chloride |
| Polymer A | | Copolymer comprising 33% by number of units derived from DIQUAT and 67% by number of units derived from acrylic acid, with a molecular mass of about 1 000 000. |
| Silicone 1 | Amodimethicone | ADM oil sold by Rhodia: Rhodorsil amine oil 21637 |
| Silicone 2 | Amodimethicone | Mirasil ADM-E amodimethicone emulsion sold by Rhodia |
| Silicone 3 | Dimethicone | Mirasil DM 500000 sold by Rhodia |
| Surfactant C | Nonionic surfactant | Rhodasurf TR6 sold by Rhodia: C13 alcohol ethoxylated 6 times. |

Example 1

Preparation of a Concentrated Ingredient "Mixture 1"

A concentrated ingredient is prepared, comprising:
25% by dry weight of Silicone 1, and
2% by dry weight of Polymer A
73% of distilled water
Mix the water and the polymer with a deflocculating paddle for 5 minutes at 700 rpm.
Add the silicone oil with stirring using the deflocculating paddle, at 700 rpm for 1 minute.

Stir the mixture for 19 minutes.
The size of the final emulsion is 7 μm. The final pH is 5.3.
Procedure:
  Mix the polymer in aqueous solution.

Example 2

Preparation of a Concentrated Ingredient "Mixture 2"

A concentrated ingredient is prepared, comprising:
23.5% of Silicone 1
0.34% of 100% acetic acid
2.34% of surfactant C (as active material)
2.34% de propylene glycol
61.2% of distilled water
2.1% of polymer A (as active material)
Procedure:
  Mix the surfactant, the propylene glycol and the water. Heat the mixture to 45-50° C.
  With stirring using a frame paddle (4 holes) at 200 rpm and at this same temperature, introduce the silicone oil, very slowly and continuously into the surfactant phase. At the end of addition, stirring is continued for 2 to 15 minutes. The size of the drops is greater than 1.5 μm.
  The emulsion thus obtained is homogenized using an Ultra-Turrax blender at 9500 rpm for 2 minutes: the emulsion is of small size (<1.5 μm).
  At room temperature, add acetic acid dropwise with stirring using the frame paddle at 400 rpm. Stirring is continued at 150 rpm for 15 minutes: an increase in viscosity is observed. The final pH is equal to 5.5.
  To 11.1 g of emulsion, stirred using a frame paddle at 400 rpm, introduce the polymer in aqueous solution, dropwise. The viscosity increases after addition of a few drops of polymer solution, lumps appear, and the mixture then becomes homogeneous.
Characterizations
  The emulsion is observed under an optical microscope: no variation in the size of the drops, the emulsion is stable and nonflocculated. The drop size is about 0.8-0.9 μm.
Storage and monitoring of the stability over time:
  Several samples are stored for monitoring the stability over time, and are placed in an oven at 45° C. for accelerated aging. The emulsion is stable after 48 hours.

Example 3

Preparation of Shampoos

Shampoos are prepared by mixing ingredients among those mentioned above, optionally with the ingredient according to the invention of Example 1.
Procedure Using the Separate Components:
1. Mix the water and the polymer
2. Add the CAPB
3. Add the anionic surfactant and then the silicone emulsion
4. Adjust the pH to 6-6.5 by adding sodium hydroxide or citric acid
5. Add the salt
Procedure using the ingredient:
1. Mix the water and the ingredient
2. Add the CAPB
3. Add the anionic surfactant
4. Adjust the pH to 6-6.5 by adding sodium hydroxide or citric acid
5. Add the salt

|  | 3.1 | 3.2 (comparative) |
|---|---|---|
| SLES (%) | 14 | 14 |
| CAPB (%) | 2 | 2 |
| NaCl (%) | 1.5 | 1.5 |
| Polymer A (%) |  | 0.2 |
| Silicone 2 (% solids) |  | 2.5 |
| Mixture 1 Example 1 | Amount such that the shampoo comprises 0.2% of polymer A and 2.5% of silicone 2 |  |
| Water | To 100% | To 100% |

Evaluations
  Measurements of deposition of silicone onto hair by X-ray fluorescence (quantification of silicon), after application of the shampoo and rinsing, show that the shampoo of Example 3.1 conditions better than the shampoo of the comparative Example 3.2C.

Example 4

Preparation of a Concentrated Ingredient "Mixture 3"

A concentrated ingredient is prepared at room temperature, comprising:
  65% of silicone 3
  1.90% of surfactant C
  26.41% of distilled water
  6.69% of polymer A (as active material).
Procedure:
Prior Preparation of a Surfactant Phase D
  Mix 70% of surfactant C and 30% of water. The mixture is heated to 45° C. and then cooled to room temperature.
  Introduce silicone 3 into an IKA reactor. Add the surfactant phase D. Mix at 400 rpm using an anchor paddle for 15 minutes.
  Using a standard stirring motor, slowly dilute the emulsion with polymer A, prepared in aqueous solution. Stir with a frame paddle at 100 rpm during the dilution. Homogenize for 5 minutes.
Characterizations
  The emulsion is observed under an optical microscope and with a Horiba granulometer. The drop size is about 0.8-1.0 μm.
  The pH of the ingredient is 3.1
  The Brookfield viscosity measured at 21° C., 10 rpm (spindle 6) is between 45 000 and 50 000 mPa·s
Storage and monitoring of the stability over time:
  Several samples are stored for monitoring of the stability over time, and placed in an oven at 45° C. for accelerated aging. The emulsion is stable after 48 hours.

Example 5

Preparation of a Concentrated Ingredient "Mixture 4"

A concentrated ingredient is prepared at room temperature, comprising:
  50% of silicone 3
  1.46% of surfactant C
  26.41% of distilled water
  10% of polymer A (as active material).

Procedure:

Prior Preparation of a Surfactant Phase D

Mix 70% of surfactant C and 30% of water. The mixture is heated to 45° C. and then cooled to room temperature.

Introduce silicone 3 into an IKA reactor. Stir the surfactant phase D. Mix at 400 rpm with an anchor paddle for 15 minutes.

Using a standard stirring motor, slowly dilute the emulsion with polymer A, prepared as an aqueous solution. Stir with a frame paddle at 100 rpm during the dilution. Homogenize for 5 minutes.

Example 6

Preparation of a Concentrated Ingredient "Mixture 5"

A concentrated ingredient is prepared at room temperature, comprising:
- 45% of silicone 3
- 2.82% of surfactant laureth-7
- 9% of polymer A (as active material)
- distilled water up to 100%.

Procedure:

The procedure is identical to the procedures mentioned above, surfactant C being replaced with laureth-7, the stirring speed and time being adjusted so as to obtain the granulometry below.

Characterizations

The emulsion is observed under an optical microscope and with a Horiba granulometer. The drop size is about 0.6 μm.

The pH of the ingredient is 2.9

The Brookfield viscosity (Brookfield DV1 machine) measured at 21° C., 10 rpm (spindle 4) is 8200 cP The emulsion is stable.

Example 7

Shampoo Formulation with Polymer A/Dimethicone/Carbopol Aqua SF1

Composition (Active Material):
- 14% SLES
- 2% CAPB
- 0.1% NaCl
- 0.2% Polymer A*.
- 1% Dimethicone*
    * introduced in the form of the mixture 5
- 1.5% Carbopol SF1

Starting Materials Used:
- Commercial name Carbopol Aqua SF1, INCI name Acrylates copolymer, 30% AM, supplier Noveon
- SLES: commercial name Empicol ESB 3M, INCI name Sodium Lauryl Ether Sulfate, 27% AM, supplier Huntsman
- CAPB: commercial name Mirataine BETC30, INCI name Cocamidopropylbetaine, 30% AM, supplier Rhodia
- Mixture 5: 5; 54% AM
- Kathon CG, supplier SEPPIC
- NaCl, supplier Prolabo The masses of the starting materials are weighed out on a balance with a precision of 0.01 g and/or on a 0.001 g precision balance.

A. Preparation Phase 1

1/ Preparation of the Water-Thickener Mixture

In a Beaker
    weigh out the mass of Carbopol Aqua SF1: 5.0 g
    weigh out and add to the liquid solution 10 g of distilled water mix with a frame paddle at 150 rpm for 5 minutes.

2/ Add the Anionic Surfactant
    weigh out the mass of SLES: 51.9 g
    add the SLES to the mixture with stirring using a frame paddle at 150 rpm, and leave to stir for 5 minutes.

3/ Structuring of the Mixture
    with gentle stirring (50 rpm), add sodium hydroxide to reach pH 6.6.

Leave to homogenize thoroughly between each addition of sodium hydroxide.

4/ Addition of the Amphoteric Surfactant
    weigh out the mass of CAPB: 6.7 g
    add the CAPB to the phase with stirring using a frame paddle at 50 rpm, and stir for the time necessary for homogenization.

B. Preparation Phase 2

1/ Dissolution of the Blend in Water

In a Beaker:
    weigh out on a 0.001 g precision balance the mass of mixture 5: 2.24 g
    weigh out and add 10 g of distilled water stir with a magnetic bar until the polymer has dissolved in the water.

2/ Addition of Salt
    weigh out on a 0.001 g precision balance the mass of salt: 0.10 g
    disperse in the mixture
    mix for 15 minutes 3/ Adjustment of the pH
    add sodium hydroxide dropwise to reach the pH region 5.5-6.5.

Leave to stir for 5 minutes.

C. Addition of Phase 2 to Phase 1

With gentle stirring using a frame paddle (50 rpm), slowly add phase 2 to the water-SLES-CAPB-Carbopol Aqua SF1 mixture.

Leave to stir until homogenized.

D. Addition of the Preserving Agent
    Incorporate 2 drops of Kathon CG
mix with a frame paddle at 150 rpm for 15 minutes.

E. Adjustment to pH 5-5.5 with Dilute Citric Acid

F. Addition of Water to Make 100 g

Characterization of the Formulation:
    pH: 5.5
    viscosity on Brookfield DV-I+viscometer, T° C.=21° C., spindle 4, RV series, speed 10 rpm:
measurement after 1 minute, 5040 mPa·s
    Satisfactory stability Example 8

Shampoo Formulation with Polymer a/Dimethicone/Carbopol ETD2020

Composition (Active Material):
- 14% SLES
- 2% CAPB
- 1% Carbopol ETD2020
- 0.2% Polymer A*
- 1% Dimethicone*
    * introduced in the form of the mixture 5

Starting Materials Used:
- Commercial name Carbopol ETD2020, INCI name Acrylates/C10-30 Alkyl Acrylate Cross-Polymer, 100% AM, supplier Noveon SLES: commercial name Empicol ESB 3M, INCI name Sodium Lauryl Ether Sulfate, 27% AM, supplier Huntsman CAPB: commercial name. Mirataine BETC30, INCI name Cocamidopropylbetaine, 30% AM, supplier Rhodia Mixture 5: 5; 54% AM Kathon CG, supplier SEPPIC NaCl, supplier Prolabo The masses of the starting materials are weighed out on a balance with a precision of 0.01 g and/or on a 0.001 g precision balance.

a. Preparation Phase 1

1/ Preparation of the Water-Thickener Mixture

In a Beaker:
weigh out 30 g of distilled water
weigh out the mass of Carbopol ETD2020: 1 g
create a vortex with a deflocculating paddle, and disperse the powder in the water
stir for 30 minutes
with gentle stirring using a frame paddle (50 rpm), add 50% sodium hydroxide to reach a pH region of 3-4

2/ Addition of the Anionic Surfactant
weigh out the mass of SLES: 51.85 g
add the SLES very gently with stirring using a frame paddle at 50 rpm, and leave to stir for 30 minutes.

3/ Addition of the Amphoteric Surfactant
weigh out the mass of CAPB: 6.7 g
add the CAPB with stirring using a frame paddle at 150 rpm, and mix for the time necessary for homogenization.

4/ Structuring of the Mixture
with gentle stirring (50 rpm), add sodium hydroxide to reach pH 5.5-6.

Leave to homogenize thoroughly between each addition of sodium hydroxide.

B. Preparation Phase 2

1/ Dissolution of the Blend in Water

In a Beaker:
weigh out on a 0.001 g precision balance the mass of mixture 5: 2.24 g
weigh out and add 5 g of distilled water
stir with a magnetic bar until the polymer has dissolved in the water.

2/ Adjustment of the pH
add 50% sodium hydroxide dropwise to reach the pH region 5.5-6.5.

Leave to stir for 5 minutes.

C. Addition of Phase 2 to Phase 1

With gentle stirring using a frame paddle (50 rpm), slowly add phase 2 to the water-SLES-CAPB-Carbopol ETD2020 mixture.

Leave to stir until homogenized.

D. Addition of the Preserving Agent

Incorporate 2 drops of Kathon CG
mix with a frame paddle at 150 rpm for 15 minutes.

E. Adjustment to pH 5-5.5 with Dilute Citric Acid

F. Addition of Water to Make 100 g

Characterization of the Formulation:
pH: 5
viscosity on Brookfield DV-I+viscometer, T° C.=21° C., spindle 4, RV series, speed 10 rpm:
measurement after 1 minute, 3540 mPa·s
Satisfactory stability Example 9

The products whose compositions are mentioned below are prepared.

The starting materials used are identified by the INCI names and/or by the commercial references. The amounts indicated are given as active material. Polymer A and the dimethicone emulsion are introduced in the form of the mixture 5.

| | Shampoo and/or shower gel | | | | | | | |
|---|---|---|---|---|---|---|---|---|
| | 1 | 2 | 3 | 4 | 5 | 6 | 7 | 8 |
| Sodium Lauryl Ether Sulfate (2EO) Empicol ® ESB-3M (Huntsman) | 14% | 14% | 10% | 10% | 14% | 14% | 10% | 12% |
| Cocamidopropyl Betaine Mirataine ® BET C-30 (Rhodia) | 2% | 2% | 2% | 2% | 2% | 2% | 2% | 3% |
| Emulsion 0.6 µm of Dimethicone: Mirasil ® DM-500 000 (Rhodia) | 1% | 1% | 1% | 1% | 1% | 1% | 1% | 1% |
| Polymer A | 0.2% | 0.3% | 0.2% | 0.3% | 0.2% | 0.3% | 0.2% | 0.3% |
| Sodium chloride | 0% | 0% | 0% | 0% | 0.1% | 0.5% | 0.1% | 0% |
| Sodium hydroxide | 0.2% | 0.2% | 0.2% | 0.2% | 0.2% | 0.2% | 0.2% | 0.2% |
| Acrylate/C$_{10-30}$ Alkyl Acrylate Crosspolymer Carbopol ® ETD-2020 (Noveon) | 1% | 1% | 1% | 1% | — | — | — | — |
| Acrylate Copolymer Carbopol ® Aqua SF-1 (Noveon) | — | — | — | — | 1.5% | 1.5% | 1.5% | — |
| Carbomer Carbopol ® 980 (Noveon) | — | — | — | — | — | — | — | 1.2% |
| Glycerine | — | 1% | — | 1% | — | 0.5% | — | 0.5% |
| Glycol Distearate, Laureth-4, Cocamidopropyl Betaine Euperlan ® PK-3000 AM (Cognis) | — | — | 1.5% | — | — | 1.5% | — | 1.5% |
| Glycol Distearate, Laureth-7, Sodium Cocoamphoacetate, Cocamidopropyl Betaine, Sodium Laureth Sulfate Mirasheen ® CP-820/G (Rhodia) | — | — | — | 2% | — | — | 2% | — |
| Citric acid | qs | qs | qs | qs | qs | qs | qs | qs |
| Fragrance, Preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

|  | Shampoo and/or shower gel | | | | | | | |
|---|---|---|---|---|---|---|---|---|
|  | 9 | 10 | 11 | 12 | 13 | 14 | 15 | 16 |
| Sodium Lauryl Ether Sulfate (2EO) Empicol ® ESB-3M (Huntsman) | 14% | 11% | 10% | 10% | 12% | 12% | 10% | 10% |
| Coco Betaine Miratainee BB-FLA (Rhodia) | 2% | — | 3% | — | — | 4% | 3% | — |
| Disodium Cocoamphodiacetate Miranol ® C2M Conc NP (Rhodia) | — | 3% | — | 3% | 4% | — | — | 2% |
| Emulsion 0.6 μm of Dimethicone: Mirasil ® DM-500 000 (Rhodia) | 1% | 1% | 1% | 1% | 1% | 1% | 1% | 1% |
| Polymer A | 0.2% | 0.2% | 0.2% | 0.2% | 0.2% | 0.2% | 0.2% | 0.2% |
| Sodium chloride | — | — | 0.5% | 0.5% | — | — | — | 1.8% |
| Sodium hydroxide | — | — | — | — | — | — | 0.5% | — |
| PEG-200 Hydrogenated Glyceryl Palmate Rewoderm ® LI 520-70 (Degussa) | 0.7% | 1.2% | — | — | 0.5% | — | — | — |
| PEG-150 Distearate Rewopal ® PEG-6000 DS (Degussa) | — | — | — | — | — | 1% | 0.4% | — |
| Xanthan gum Rhodicare ® XC (Rhodia) | — | — | 0.6% | 0.6% | 0.6% | — | — | — |
| Hydroxyethyl cellulose Natrosol ® 250-HHR HEC (Aqualon) | — | — | — | — | — | — | 1% | — |
| Hydroxypropyl Guar Jaguar ® HP-105 (Rhodia) | — | — | — | — | — | — | — | 0.8% |
| Propylene Glycol | 0.3% | 0.3% | — | — | — | 0.4% | 0.3% | 0.3% |
| Glycol Distearate, Laureth-4, Cocamidopropyl Betaine Euperlan ® PK-3000 AM (Cognis) | 1.5% | — | 1.5% | — | — | 1.5% | — | 1.5% |
| Citric acid | qs | qs | qs | qs | qs | qs | qs | qs |
| Fragrance, Preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

|  | 17 | 18 | 19 | 20 | 21 | 22 | 23 | 24 |
|---|---|---|---|---|---|---|---|---|
| Sodium Lauryl Ether Sulfate (2EO) Empicol ® ESB-3M (Huntsman) | 14% | 11% | 10% | 10% | 12% | 12% | 10% | 10% |
| Disodium Cocoamphodiacetate Miranol ® C2M Conc NP (Rhodia) | 2% | 3% | 2% | 3% | 4% | 2% | 2% | 2% |
| Emulsion 0.6 μm of Dimethicone: Mirasil ® DM-500 000 (Rhodia) | 1% | 1% | 1% | 1% | 1% | 1% | 1% | 1% |
| Polymer A | 0.2% | 0.2% | 0.2% | 0.2% | 0.2% | 0.2% | 0.2% | 0.2% |
| Sodium chloride | 0.2% | 0.15% | 0.1% | 0.15% | 0.15% | 0.15% | 0.15% | 0.15% |
| Sodium hydroxide | 0.2% | 0.2% | 0.2% | 0.2% | 0.2% | 0.2% | 0.2% | 0.2% |
| Acrylate/C$_{10-30}$ Alkyl Acrylate Crosspolymer Carbopol ® ETD-2020 (Noveon) | 1% | 1% | 1% | 1% | 1% | 1% | 1% | 1% |
| Guar Hydroxypropyltrimonium Chloride Jaguar ® C-13S (Rhodia) | 0.1% | — | — | — | — | — | — | — |
| Guar Hydroxypropyltrimonium Chloride Jaguar ® Excel (Rhodia) | — | 0.1% | — | 0.1% | — | — | — | — |
| Hydroxypropyl Guar Hydroxypropyltrimonium Chloride Jaguar ® C-162 (Rhodia) | — | — | 0.3% | — | — | — | — | — |
| Polyquaternium-10 Ucare Polymer ® JR-400 (Amerchol) | — | — | — | 0.1% | 0.3% | — | — | — |
| Polyquaternium-7 Merquat ® 550 (Nalco) | — | — | — | — | — | 0.3% | — | — |
| Polyquaternium-11 Mirapol ® PQ-11 (Rhodia) | — | — | — | — | — | — | 0.05% | — |
| Polyquaternium-22 Merquat ® 280 (Nalco) | — | — | — | — | — | — | — | 0.1% |
| Glycol Distearate, Laureth-4, Cocamidopropyl Betaine Euperlan ® PK-3000 AM (Cognis) | 1.5% | — | — | — | 1.5% | — | 1.5% | 1.5% |
| Citric acid | qs | qs | qs | qs | qs | qs | qs | qs |
| Fragrance, Preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

|  | 25 | 26 | 27 | 28 | 29 | 30 | 31 | 32 |
|---|---|---|---|---|---|---|---|---|
| Anionic surfactant: Sodium Lauryl Ether Sulfate (2EO) Empicol ® ESB-3M (Huntsman) | 14% | 11% | 10% | 10% | 12% | 12% | 10% | 10% |

| Shampoo and/or shower gel | | | | | | | | |
|---|---|---|---|---|---|---|---|---|
| Cocamidopropyl Betaine Mirataine ® BET C-30 (Rhodia) | 2% | — | 3% | — | — | 4% | 3% | 3% |
| Emulsion 0.6 µm of Dimethicone: Mirasil ® DM-500 000 (Rhodia) | 1% | 1% | 1% | 1% | 1% | 1% | 1% | 1% |
| Polymer A | 0.2% | 0.2% | 0.2% | 0.2% | 0.2% | 0.2% | 0.2% | 0.2% |
| Sodium chloride | 0.1% | 0.1% | 0.1% | — | 0.1% | — | — | — |
| Acrylate Copolymer Carbopol ® Aqua SF-1 (Noveon) | 1.5% | 1.5% | 1.5% | 1.5% | 1.5% | 1.5% | 1.5% | 1.5% |
| Sodium hydroxide | 0.2% | 0.2% | 0.2% | 0.2% | 0.2% | 0.2% | 0.2% | 0.2% |
| Guar Hydroxypropyltrimonium Chloride Jaguar ® C-13S (Rhodia) | 0.1% | — | — | 0.1% | — | — | — | — |
| Polyquaternium-10 Ucare Polymer ® JR-400 (Amerchol) | — | 0.3% | — | — | — | — | — | — |
| Polyquaternium-39 Merquat ® Plus 3330 (Nalco) | — | — | 0.3% | — | — | — | — | — |
| Polyquaternium-44 Luviquat ® UltraCare (BASF) | — | — | — | 0.1% | 0.1% | — | — | — |
| Polyquaternium-67 SoftCAT ® Polymer SL (Amerchol) | — | — | — | — | — | 0.2% | — | — |
| Polymethacrylamidopropyltrimonium Chloride Polycare 133 (Rhodia) | — | — | — | — | — | — | 0.2% | — |
| Acrylamidopropyltrimonium Chloride/ Acrylamide Copolymer Salcare ® SC-60 (Ciba SC) | — | — | — | — | — | — | — | 0.3% |
| Glycol Distearate, Laureth-4, Cocamidopropyl Betaine Euperlan ® PK-3000 AM (Cognis) | 1.5% | 1.5% | 1.5% | 1.5% | 1.5% | 1.5% | 1.5% | 1.5% |
| Citric acid | qs | qs | qs | qs | qs | qs | qs | qs |
| Fragrance, Preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

| | 41 | 42 | 43 | 44 | 45 | 46 | 47 | 48 |
|---|---|---|---|---|---|---|---|---|
| Sodium Lauryl Ether Sulfate (2EO) Empicol ® ESB-3M (Huntsman) | — | 10% | 6% | — | 12% | 12% | — | 14% |
| Ammonium Lauryl Sulfate Rhodapon ® L-22 (Rhodia) | 5% | — | 6% | 7% | — | — | 5% | — |
| Ammonium Lauryl Ether Sulfate (2E0) Rhodapex ® EA-2 (Rhodia) | — | — | — | 7% | — | — | 7% | — |
| Disodium Cocoamphodiacetate Miranol ® C2M Conc NP (Rhodia) | 3% | — | — | — | — | 3% | — | 1% |
| Cocamidopropyl Betaine Mirataine ® BET C-30 (Rhodia) | — | 4% | — | — | 3% | — | 2% | 2% |
| Disodium Laureth Sulfosuccinate Geropon ® SBFA-30 (Rhodia) | 6% | — | 2% | — | 2% | — | — | — |
| Sodium Lauroyl Glutamate Protelan ® AGL-95 (Zschimmer & Schwarz) | — | 2% | — | — | — | — | — | 2% |
| Coco Glucoside Plantacare ® 818 UP (Cognis) | 2% | — | — | 1% | — | 2% | — | — |
| Cocamide MIPA Empilan ® CIS (Huntsman) | 1% | — | 1.5% | — | 1% | — | 1% | 1% |
| Laureth-2 Empilan ® KBE-2 (Huntsman) | — | 1% | — | — | — | — | — | — |
| Sodium Lauroyl Sarcosinate Protelan ® LS-9011 (Zschimmer & Schwarz) | — | — | — | 1% | — | — | 2% | — |
| Emulsion 0.6 µm of Dimethicone: Mirasil ® DM-500 000 (Rhodia) | 1% | 1% | 1% | 1% | 1% | 1% | 1% | 1% |
| Polymer A | 0.2% | 0.2% | 0.2% | 0.2% | 0.2% | 0.2% | 0.2% | 0.2% |
| Sodium hydroxide | 0.2% | 0.2% | 0.2% | 0.2% | — | 0.2% | 0.2% | — |
| Sodium chloride | 0.1% | 0.1% | 0.2% | 0.1% | 1.6% | 0.3% | 0.1% | 1.2% |
| Acrylate/$C_{10-30}$ Alkyl Acrylate Crosspolymer Carbopol ® ETD-2020 (Noveon) | 1% | 1% | 1% | 1% | — | — | — | — |
| Acrylate Copolymer Carbopol ® Aqua SF-1 (Noveon) | — | — | — | — | 1.5% | 1.5% | 1.5% | 1.5% |
| Glycol Distearate, Laureth-4, Cocamidopropyl Betaine Euperlan ® PK-3000 AM (Cognis) | — | — | — | 1.5% | — | 1.5% | — | 1.5% |
| Citric acid | qs | qs | qs | qs | qs | qs | qs | qs |
| Fragrance, Preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

| Shampoo and/or shower gel | | | | | |
|---|---|---|---|---|---|
| | 57 | 58 | 59 | 60 | 61 |
| Sodium Lauryl Ether Sulfate (2EO) Empicol ® ESB-3M (Huntsman) | 10% | 10% | 14% | 10% | 12% |
| Cocamidopropyl Betaine Mirataine ® BET C-30 (Rhodia) | 2% | 2% | 2% | 2% | 3% |
| Emulsion 0.6 μm of Dimethicone: Mirasil ® DM-500 000 (Rhodia) | 1% | 1% | 1% | 1% | 1% |
| Polymer A | 0.2% | 0.3% | 0.3% | 0.2% | 0.3% |
| Sodium Chloride | 0% | 0% | 0.5% | 0.1% | 0% |
| Sodium hydroxide | 0.2% | 0.2% | 0.2% | 0.2% | 0.2% |
| Acrylate/C$_{10-30}$ Alkyl Acrylate Crosspolymer Carbopol ® ETD-2020 (Noveon) | 1% | 1% | — | — | — |
| Acrylate Copolymer Carbopol ® Aqua SF-1 (Noveon) | — | — | 1.5% | 1.5% | — |
| Carbomer Carbopol ® 980 (Noveon) | — | — | — | — | 1.2% |
| Glycerine | — | 1% | 0.5% | — | 0.5% |
| Sodium Laureth Sulfate, Glycol Distearate Cocamide MEA, Laureth-10 Euperlan PK-771 BENZ (Cognis) | 1.5% | — | 1.5% | — | 1.5% |
| PEG-3 Distearate Genapol TS (Clariant) | — | 1.5% | — | 1.5% | — |
| Citric acid | qs | qs | qs | qs | qs |
| Fragrance, Preserving agents | qs | qs | qs | qs | qs |
| Demineralized water | qsp 100% | qsp 100% | qsp 100% | qsp 100% | qsp 100% |

| | 62 | 63 | 64 | 65 | 66 | 67 | 68 | 69 |
|---|---|---|---|---|---|---|---|---|
| Sodium Lauryl Ether Sulfate (2EO) Empicol ® ESB-3M (Huntsman) | 14% | 10% | 12% | 10% | 14% | 10% | 12% | 10% |
| Coco Betaine Mirataine ® BB-FLA (Rhodia) | 2% | 3% | 4% | — | 2% | 3% | 4% | — |
| Disodium Cocoamphodiacetate Miranol ® C2M Conc NP (Rhodia) | — | — | — | 2% | — | — | — | 2% |
| Emulsion 0.6 μm of Dimethicone: Mirasil ® DM-500 000 (Rhodia) | 1% | 1% | 1% | 1% | 1% | 1% | 1% | 1% |
| Polymer A | 0.2% | 0.2% | 0.2% | 0.2% | 0.2% | 0.2% | 0.2% | 0.2% |
| Sodium chloride | — | 0.5% | — | 1.8% | — | 0.5% | — | 1.8% |
| Sodium hydroxide | — | — | — | — | — | — | — | — |
| PEG-200 Hydrogenated Glyceryl Palmate Rewoderm ® LI 520-70 (Degussa) | 0.7% | — | — | — | 0.7% | — | — | — |
| PEG-150 Distearate Rewopal ® PEG-6000 DS (Degussa) | — | — | 1% | — | — | — | 1% | — |
| Xanthan gum Rhodicare ® XC (Rhodia) | — | 0.6% | — | — | — | 0.6% | — | — |
| Hydroxyethyl cellulose Natrosol ® 250-HHR HEC (Aqualon) | — | — | — | — | — | — | — | — |
| Hydroxypropyl Guar Jaguar ® HP-105 (Rhodia) | — | — | — | 0.8% | — | — | — | 0.8% |
| Propylene Glycol | 0.3% | — | 0.4% | 0.3% | 0.3% | — | 0.4% | 0.3% |
| Sodium Laureth Sulfate, Glycol Distearate Cocamide MEA, Laureth-10 Euperlan PK-771 BENZ (Cognis) | 1.0% | 1.0% | 1.0% | 1.0% | — | — | — | — |
| PEG-3 Distearate Genapol TS (Clariant) | — | — | — | — | 1.5% | 1.5% | 1.5% | 1.5% |
| Citric acid | qs | qs | qs | qs | qs | qs | qs | qs |
| Fragrance, Preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

| | 70 | 71 | 72 | 73 | 74 | 75 | 76 | 77 |
|---|---|---|---|---|---|---|---|---|
| Sodium Lauryl Ether Sulfate (2EO) Empicol ® ESB-3M (Huntsman) | 14% | 12% | 10% | 10% | 14% | 12% | 10% | 10% |
| Disodium Cocoamphodiacetate Miranol ® C2M Conc NP (Rhodia) | 2% | 4% | 2% | 2% | 2% | 4% | 2% | 2% |
| Emulsion 0.6 μm of Dimethicone: Mirasil ® DM-500 000 (Rhodia) | 1% | 1% | 1% | 1% | 1% | 1% | 1% | 1% |
| Polymer A | 0.2% | 0.2% | 0.2% | 0.2% | 0.2% | 0.2% | 0.2% | 0.2% |

Shampoo and/or shower gel

| | | | | | | | | |
|---|---|---|---|---|---|---|---|---|
| Sodium chloride | 0.2% | 0.15% | 0.15% | 0.15% | 0.2% | 0.15% | 0.15% | 0.15% |
| Sodium hydroxide | 0.2% | 0.2% | 0.2% | 0.2% | 0.2% | 0.2% | 0.2% | 0.2% |
| Acrylate/$C_{10\text{-}30}$ Alkyl Acrylate Crosspolymer Carbopol® ETD-2020 (Noveon) | 1% | 1% | 1% | 1% | 1% | 1% | 1% | 1% |
| Guar Hydroxypropyltrimonium Chloride Jaguar® C-13S (Rhodia) | 0.1% | — | — | — | 0.1% | — | — | — |
| Guar Hydroxypropyltrimonium Chloride Jaguar® Excel (Rhodia) | — | — | — | — | — | — | — | — |
| Hydroxypropyl Guar Hydroxypropyltrimonium Chloride Jaguar® C-162 (Rhodia) | — | — | — | — | — | — | — | — |
| Polyquaternium-10 Ucare Polymer® JR-400 (Amerchol) | — | 0.3% | — | — | — | 0.3% | — | — |
| Polyquaternium-7 Merquat® 550 (Nalco) | — | — | — | — | — | — | — | — |
| Polyquaternium-11 Mirapol® PQ-11 (Rhodia) | — | — | 0.05% | — | — | — | 0.05% | — |
| Polyquaternium-22 Merquat® 280 (Nalco) | — | — | — | 0.1% | — | — | — | 0.1% |
| Sodium Laureth Sulfate, Glycol Distearate Cocamide MEA, Laureth-10 Euperlan PK-771 BENZ (Cognis) | 1.5% | 1.5% | 1.5% | 1.5% | — | — | — | — |
| PEG-3 Distearate Genapol TS (Clariant) | — | — | — | — | 1.5% | 1.5% | 1.5% | 1.5% |
| Citric acid | qs | qs | qs | . qs | qs | qs | qs | qs |
| Fragrance, Preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

| | 78 | 79 | 80 | 81 | 82 | 83 | 84 | 85 |
|---|---|---|---|---|---|---|---|---|
| Anionic surfactant: Sodium Lauryl Ether Sulfate (2EO) Empicol® ESB-3M (Huntsman) | 14% | 11% | 10% | 10% | 12% | 12% | 10% | 10% |
| Cocamidopropyl Betaine Mirataine® BET C-30 (Rhodia) | 2% | — | 3% | — | — | 4% | 3% | 3% |
| Emulsion 0.6 μm of Dimethicone: Mirasil® DM-500 000 (Rhodia) | 1% | 1% | 1% | 1% | 1% | 1% | 1% | 1% |
| Polymer A | 0.2% | 0.2% | 0.2% | 0.2% | 0.2% | 0.2% | 0.2% | 0.2% |
| Sodium chloride | 0.1% | 0.1% | 0.1% | — | 0.1% | — | — | — |
| Acrylate Copolymer Carbopol® Aqua SF-1 (Noveon) | 1.5% | 1.5% | 1.5% | 1.5% | 1.5% | 1.5% | 1.5% | 1.5% |
| Sodium hydroxide | 0.2% | 0.2% | 0.2% | 0.2% | 0.2% | 0.2% | 0.2% | 0.2% |
| Guar Hydroxypropyltrimonium Chloride Jaguar® C-13S (Rhodia) | 0.1% | — | — | 0.1% | — | — | — | — |
| Polyquaternium-10 Ucare Polymer® JR-400 (Amerchol) | — | 0.3% | — | — | — | — | — | — |
| Polyquaternium-39 Merquat® Plus 3330 (Nalco) | — | — | 0.3% | — | — | — | — | — |
| Polyquaternium-44 Luviquat® UltraCare (BASF) | — | — | — | 0.1% | 0.1% | — | — | — |
| Polyquaternium-67 SoftCAT® Polymer SL (Amerchol) | — | — | — | — | — | 0.2% | — | — |
| Polymethacrylamidopropyltrimonium Chloride Polycare 133 (Rhodia) | — | — | — | — | — | — | 0.2% | — |
| Acrylamidopropyltrimonium Chloride/Acrylamide Copolymer Salcare® SC-60 (Ciba SC) | — | — | — | — | — | — | — | 0.3% |
| Sodium Laureth Sulfate, Glycol distearate Cocamide MEA, Laureth-10 Euperlan PK-771 BENZ (Cognis) | 1.5% | 1.5% | 1.5% | 1.5% | 1.5% | 1.5% | 1.5% | 1.5% |
| Citric acid | qs | qs | qs | qs | qs | qs | qs | qs |
| Fragrance, Preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

| Shampoo and/or shower gel | | | | | | | | |
|---|---|---|---|---|---|---|---|---|
| | 86 | 87 | 88 | 89 | 90 | 91 | 92 | 93 |
| Anionic surfactant: | | | | | | | | |
| Sodium Lauryl Ether Sulfate (2EO) Empicol ® ESB-3M (Huntsman) | 14% | 11% | 10% | 10% | 12% | 12% | 10% | 10% |
| Cocamidopropyl Betaine Mirataine ® BET-C-30 (Rhodia) | 2% | — | 3% | — | — | 4% | 3% | 3% |
| Emulsion 0.6 μm of Dimethicone: Mirasil ® DM-500 000 (Rhodia) | 1% | 1% | 1% | 1% | 1% | 1% | 1% | 1% |
| Polymer A | 0.2% | 0.2% | 0.2% | 0.2% | 0.2% | 0.2% | 0.2% | 0.2% |
| Sodium chloride | 0.1% | 0.1% | 0.1% | — | 0.1% | — | — | — |
| Acrylate Copolymer Carbopol ® Aqua SF-1 (Noveon) | 1.5% | 1.5% | 1.5% | 1.5% | 1.5% | 1.5% | 1.5% | 1.5% |
| Sodium hydroxide | 0.2% | 0.2% | 0.2% | 0.2% | 0.2% | 0.2% | 0.2% | 0.2% |
| Guar Hydroxypropyltrimonium Chloride Jaguar ® C-13S (Rhodia) | 0.1% | — | — | 0.1% | — | — | — | — |
| Polyquaternium-10 Ucare Polymer ® JR-400 (Amerchol) | — | 0.3% | — | — | — | — | — | — |
| Polyquaternium-39 Merquat ® Plus 3330 (Nalco) | — | — | 0.3% | — | — | — | — | — |
| Polyquaternium-44 Luviquat ® UltraCare (BASF) | — | — | — | 0.1% | 0.1% | — | — | — |
| Polyquaternium-67 SoftCAT ® Polymer SL (Amerchol) | — | — | — | — | — | 0.2% | — | — |
| Polymethacrylamidopropyltrimonium Chloride Polycare 133 (Rhodia) | — | — | — | — | — | — | 0.2% | — |
| Acrylamidopropyltrimonium Chloride/ Acrylamide Copolymer Salcare ® SC-60 (Ciba SC) | — | — | — | — | — | — | — | 0.3% |
| PEG-3 Distearate Genapol TS (Clariant) | 1.5% | 1.5% | 1.5% | 1.5% | 1.5% | 1.5% | 1.5% | 1.5% |
| Citric acid | qs | qs | qs | qs | qs | qs | qs | qs |
| Fragrance, Preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

| | 100 | 101 | 102 | 103 | 104 | 105 |
|---|---|---|---|---|---|---|
| Sodium Lauryl Ether Sulfate (2E0) Empicol ® ESB-3M (Huntsman) | — | 12% | 14% | — | 12% | 14% |
| Ammonium Lauryl Sulfate Rhodapon ® L-22 (Rhodia) | 7% | — | — | 7% | — | — |
| Ammonium Lauryl Ether Sulfate (2EO) Rhodapex ® EA-2 (Rhodia) | 7% | — | — | 7% | — | — |
| Disodium Cocoamphodiacetate Miranol ® C2M Conc NP (Rhodia) | — | 3% | 1% | — | 3% | 1% |
| Cocamidopropyl Betaine Mirataine ® BET C-30 (Rhodia) | — | — | 2% | — | — | 2% |
| Disodium Laureth Sulfosuccinate Geropon ® SBFA-30 (Rhodia) | — | — | — | — | — | — |
| Sodium Lauroyl Glutamate Protelan ® AGL-95 (Zschimmer & Schwarz) | — | — | 2% | — | — | 2% |
| Coco Glucoside Plantacare ® 818 UP (Cognis) | 1% | 2% | — | 1% | 2% | — |
| Cocamide MIPA Empilan ® CIS (Huntsman) | — | — | 1% | — | — | 1% |
| Laureth-2 Empilan ® KBE-2 (Huntsman) | — | — | — | — | — | — |
| Sodium Lauroyl Sarcosinate Protelan ® LS-9011 (Zschimmer & Schwarz) | 1% | — | — | 1% | — | — |
| Emulsion 0.6 μm of Dimethicone: Mirasil ® DM-500 000 (Rhodia) | 1% | 1% | 1% | 1% | 1% | 1% |
| Polymer A | 0.2% | 0.2% | 0.2% | 0.2% | 0.2% | 0.2% |
| Sodium hydroxide | 0.2% | 0.2% | — | 0.2% | 0.2% | — |
| Sodium chloride | 0.1% | 0.3% | 1.2% | 0.1% | 0.3% | 1.2% |
| Acrylate/C$_{10-30}$ Alkyl Acrylate Cross-polymer Carbopol ® ETD-2020 (Noveon) | 1% | — | — | 1% | — | — |
| Acrylate Copolymer Carbopol ® Aqua SF-1 (Noveon) | — | 1.5% | 1.5% | — | 1.5% | 1.5% |

-continued

| Shampoo and/or shower gel | | | | | | |
|---|---|---|---|---|---|---|
| Sodium Laureth Sulfate, Glycol Distearate Cocamide MEA, Laureth-10 Euperlan PK-771 BENZ (Cognis) | 1.5% | 1.5% | 1.5% | — | — | — |
| PEG-3 Distearate Genapol TS (Clariant) | — | — | — | 1.5% | 1.5% | 1.5% |
| Citric acid | qs | qs | qs | qs | qs | qs |
| Fragrance, Preserving agents | qs | qs | qs | qs | qs | qs |
| Demineralized water | qsp 100% | qsp 100% | qsp 100% | qsp 100% | qsp 100% | qsp 100% |

The invention claimed is:

1. A concentrated ingredient for treating and/or modifying surfaces, comprising:
a) a conditioning agent,
b) an ampholytic copolymer comprising:
0.1% to 50% of the units of said copolymer are units $B_{CAT}$ derived from the polymerization of at least one monomer compound $B_{CAT}$ of general formula I:

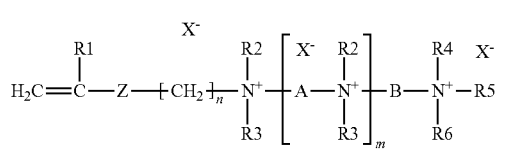

in which:
$R_1$ is a hydrogen atom or a methyl or ethyl group;
$R_2$, $R_3$, $R_4$, $R_5$ and $R_6$, which are identical or different, are linear or branched $C_1$-$C_6$ and optionally $C_1$-$C_4$ alkyl, hydroxyalkyl or aminoalkyl groups,
m is an integer from 0 to 10;
n is an integer from 1 to 6;
Z represents a —C(O)O— or —C(O)NH— group or an oxygen atom;
A represents a group $(CH_2)_p$, p being an integer from 1 to 6;
B represents a linear or branched $C_2$-$C_{12}$ polymethylene chain, optionally interrupted with one or more heteroatoms or hetero groups, and optionally substituted with one or more hydroxyl or amino groups,
$X^-$, which are identical or different, represent counterions;
and 50% to 99.9% of the units of said copolymer are units $B_A$ and, optionally, units $B_N$,
said units $B_A$ being derived from the polymerization of at least one hydrophilic monomer $B_A$ bearing a function of acidic nature that is copolymerizable with $B_{CAT}$, which is anionic or potentially anionic;
and said units $B_N$ being derived from at least one ethylenically unsaturated monomer $B_N$ of neutral charge bearing one or more hydrophilic groups, which is copolymerizable with $B_{CAT}$ and $B_A$;
wherein the total amount of units $B_A$ and optionally $B_N$ being from 50% to 99.9% by number,
c) optionally a surfactant, and
d) optionally water,
wherein:
the total weight amount of products a) and b) in the ingredient is at least 10%, and
the weight ratio of product c), if it is present, to product a) is less than 1.0.

2. The ingredient as claimed in claim 1, having an amount of water less than 90% by weight.

3. The ingredient as claimed in claim 1, having a weight ratio between product b) and product a) in the concentrated ingredient of 0.05 and 9.

4. The ingredient as claimed in claim 1, presenting:
from 10% to 75% by weight of product a),
from 0.5% to 20% by weight of product b),
from 0 to 15% by weight of product c), and
optionally water.

5. The ingredient as claimed in claim 1, comprising water, and wherein that water is in the form of a direct emulsion comprising droplets of the conditioning agent a) dispersed in water.

6. The ingredient as claimed in claim 5, wherein the emulsion is an emulsion whose mean droplet size is greater than or equal to 2 µm.

7. The ingredient as claimed in claim 5, wherein the emulsion is an emulsion whose mean droplet size is between 0.15 µm and 2 µm.

8. The ingredient as claimed in claim 5, wherein the emulsion is an emulsion whose mean droplet size is less than or equal to 0.15 µm.

9. The ingredient as claimed in claim 1, wherein the conditioning agent a) is a water-insoluble nonvolatile oil.

10. The ingredient as claimed in claim 1, wherein the conditioning agent comprises:
a1) plant, mineral or animal oils, or
a2) polyorganosiloxanes.

11. The ingredient as claimed in claim 10, wherein the polyorganosiloxane a2) comprises a polydimethylorganosiloxanesiloxane, or a polyorganosiloxane comprising amine groups, quaternary ammonium groups, hydroxyl groups, polyoxyalkylene groups, or aromatic groups.

12. The ingredient as claimed in claim 1, wherein:
the units $B_{CAT}$ are derived from the monomer $B_{CAT}$ having the following formula:

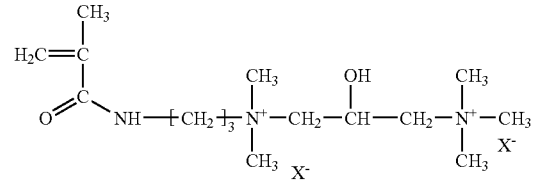

$X^-$ representing a chloride or methyl sulfate ion,
the units $B_A$ are derived from acrylic acid,
the polymer does not comprise any units $B_N$, and
the numerical ratio between the units $B_A$ and the units $B_{CAT}$ is from 50/50 to 90/10.

13. The ingredient as claimed in claim 1, wherein the surfactant c) is a nonionic surfactant.

14. The concentrated ingredient as claimed in claim 1, having a total weight amount of products a) and b) in the ingredient of at least 60%.

15. The concentrated ingredient as claimed in claim 1, having a weight ratio between product c), if it is present, and product a) of less than 0.1.

16. The ingredient as claimed in claim 1, having an amount of water less than 75% by weight.

17. The ingredient as claimed in claim 1, having a weight ratio between product b) and product a) in the concentrated ingredient of between 0.075 and 0.3.

18. The ingredient as claimed in claim 1, presenting:
from 20% to 70% by weight of product a),
from 1% to 15% by weight of product b),
from 0 to 15% by weight of product c), and
optionally water.

19. The ingredient as claimed claim 1, wherein said ampholytic copolymer is one wherein:
m is an integer from 0 to 2;
n is an integer from 2 to 4;
and p is an integer from 2 to 4.

20. The ingredient as claimed in claim 1, wherein the surfactant c) is an ethoxylated alcohol.

21. The concentrated ingredient of claim 1, wherein the ingredient comprises 0% to 2.82% by weight of the surfactant c).

22. The concentrated ingredient of claim 21, wherein the ingredient comprises 1.46% to 2.82% by weight of the surfactant c).

23. The concentrated ingredient of claim 1, wherein the ingredient comprises 0% by weight of the surfactant c).

24. A cosmetic composition for treating and/or modifying surfaces made by preparing a concentrated ingredient comprising:
a) a conditioning agent, and
b) an ampholytic copolymer comprising:
0.1% to 50% of the units of said copolymer are units $B_{CAT}$ derived from the polymerization of at least one monomer compound $B_{CAT}$ of general formula I:

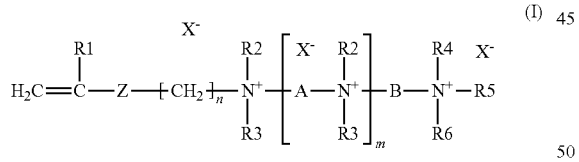

in which:
$R_1$ is a hydrogen atom or a methyl or ethyl group;
$R_2$, $R_3$, $R_4$, $R_5$ and $R_6$, which are identical or different, are linear or branched $C_1$-$C_6$ and optionally $C_1$-$C_4$ alkyl, hydroxyalkyl or aminoalkyl groups,
m is an integer from 0 to 10;
n is an integer from 1 to 6;
Z represents a —C(O)O— or —C(O)NH— group or an oxygen atom;
A represents a group $(CH_2)_p$, p being an integer from 1 to 6;
B represents a linear or branched $C_2$-$C_{12}$ polymethylene chain, optionally interrupted with one or more heteroatoms or hetero groups, especially 0 or NH, and optionally substituted with one or more hydroxyl or amino groups,
$X^-$, which are identical or different, represent counterions;
and 50% to 99.9% of the units of said copolymer are units $B_A$ and, optionally, units $B_N$,
said units $B_A$ being derived from the polymerization of at least one hydrophilic monomer $B_A$ bearing a function of acidic nature that is copolymerizable with $B_{CAT}$, which is anionic or potentially anionic;
and said units $B_N$ being derived from at least one ethylenically unsaturated monomer $B_N$ of neutral charge bearing one or more hydrophilic groups, which is copolymerizable with $B_{CAT}$ and $B_A$;
wherein the total amount of units $B_A$ and optionally $B_N$ being from 50% to 99.9% by number,
wherein:
the total amount of products a) and b) by weight in said ingredient is at least 10%, and
formulating said cosmetic composition with said concentrated ingredient
wherein said cosmetic composition optionally comprises:
c) a surfactant, and/or
d) water,
further wherein the weight ratio of product c), if it is present, to product a), is less than 1.0.

25. A concentrated ingredient for treating and/or modifying surfaces consisting of:
a) a conditioning agent,
b) an ampholytic copolymer comprising:
0.1% to 50% of the units of said copolymer are units $B_{CAT}$ derived from the polymerization of at least one monomer compound $B_{CAT}$ of general formula I:

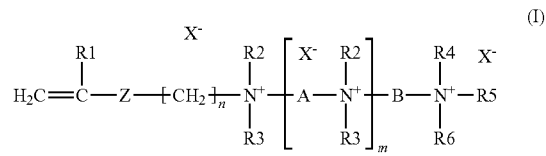

in which:
$R_1$ is a hydrogen atom or a methyl or ethyl group;
$R_2$, $R_3$, $R_4$, $R_5$ and $R_6$, which are identical or different, are linear or branched $C_1$-$C_6$ and optionally $C_1$-$C_4$ alkyl, hydroxyalkyl or aminoalkyl groups,
m is an integer from 0 to 10;
n is an integer from 1 to 6;
Z represents a —C(O)O— or —C(O)NH— group or an oxygen atom;
A represents a group $(CH_2)_p$, p being an integer from 1 to 6;
B represents a linear or branched $C_2$-$C_{12}$ polymethylene chain, optionally interrupted with one or more heteroatoms or hetero groups, and optionally substituted with one or more hydroxyl or amino groups,
$X^-$, which are identical or different, represent counterions;
and 50% to 99.9% of the units of said copolymer are units $B_A$ and, optionally, units $B_N$,
said units $B_A$ being derived from the polymerization of at least one hydrophilic monomer $B_A$ bearing a function of acidic nature that is copolymerizable with $B_{CAT}$, which is anionic or potentially anionic;
and said units $B_N$ being derived from at least one ethylenically unsaturated monomer $B_N$ of neutral charge bearing one or more hydrophilic groups, which is copolymerizable with $B_{CAT}$ and $B_A$;

wherein the total amount of units $B_A$ and optionally $B_N$ being from 50% to 99.9% by number,
  c) optionally a surfactant, and
  d) optionally water,
  wherein:
    the total weight amount of products a) and b) in the ingredient is at least 10%, and
    the weight ratio of product c), if it is present, to product a) is less than 1.0.

* * * * *